(12) United States Patent
Gomi et al.

(10) Patent No.: US 10,709,530 B2
(45) Date of Patent: Jul. 14, 2020

(54) PHOTOCURABLE COMPOSITION, DENTURE BASE, AND PLATE DENTURE

(71) Applicant: MITSUI CHEMICALS, INC., Minato-ku, Tokyo (JP)

(72) Inventors: Toshikazu Gomi, Ichihara (JP); Takashi Koura, Iwakuni (JP); Hirohisa Shiode, Yokohama (JP); Mai Kimura, Ichihara (JP)

(73) Assignee: MITSUI CHEMICALS, INC., Minato-Ku, Tokyo (JP)

( * ) Notice: Subject to any disclaimer, the term of this patent is extended or adjusted under 35 U.S.C. 154(b) by 245 days.

(21) Appl. No.: 15/547,217

(22) PCT Filed: Feb. 1, 2016

(86) PCT No.: PCT/JP2016/052961
§ 371 (c)(1),
(2) Date: Jul. 28, 2017

(87) PCT Pub. No.: WO2016/125758
PCT Pub. Date: Aug. 11, 2016

(65) Prior Publication Data
US 2018/0014919 A1    Jan. 18, 2018

(30) Foreign Application Priority Data

Feb. 3, 2015  (JP) ................... 2015-019541
Feb. 3, 2015  (JP) ................... 2015-019542
Feb. 3, 2015  (JP) ................... 2015-019543

(51) Int. Cl.
| | |
|---|---|
| *A61C 13/01* | (2006.01) |
| *A61K 6/00* | (2020.01) |
| *A61K 6/887* | (2020.01) |
| *A61C 13/00* | (2006.01) |
| *A61C 13/10* | (2006.01) |

(52) U.S. Cl.
CPC .......... *A61C 13/01* (2013.01); *A61C 13/0013* (2013.01); *A61C 13/1003* (2013.01); *A61K 6/00* (2013.01); *A61K 6/887* (2020.01)

(58) Field of Classification Search
CPC . A61C 13/0013; A61C 13/01; A61C 13/1003; A61K 6/083; A61K 6/00
See application file for complete search history.

(56) References Cited

U.S. PATENT DOCUMENTS

| | | |
|---|---|---|
| 2002/0127345 A1 | 9/2002 | Rheinberger et al. |
| 2006/0100298 A1 | 5/2006 | Ulrich et al. |
| 2009/0004579 A1 | 1/2009 | Sarmah et al. |

FOREIGN PATENT DOCUMENTS

| | | |
|---|---|---|
| JP | 56-161313 A | 12/1981 |
| JP | 6-78937 A | 3/1994 |
| JP | 2003-85832 A | 3/2003 |
| JP | 4160311 B2 | 10/2008 |
| WO | 01/12679 A1 | 2/2001 |

OTHER PUBLICATIONS

Database WPI; AN 1982-06723E, XP002784785 & JP S56 161313 cited in the International Search Report (6 pages).
Extended Search Report issued by the European Patent Office in corresponding European Patent Application No. 16746589.7-1132 dated Oct. 10, 2018 (9 pages).
International Search Report (PCT/ISA/210) dated May 10, 2016, by the Japanese Patent Office as the International Searching Authority for International Application No. PCT/JP2016/052961.
Written Opinion (PCT/ISA/237) dated May 10, 2016, by the Japanese Patent Office as the International Searching Authority for International Application No. PCT/JP2016/052961.

*Primary Examiner* — Ralph A Lewis
(74) *Attorney, Agent, or Firm* — Buchanan Ingersoll & Rooney PC

(57) ABSTRACT

The present invention provides a photocurable composition which is used for the production by stereolithography of a dental prosthesis or the like. This photocurable composition contains a (meth)acrylic monomer component and a photopolymerization initiator; and the (meth)acrylic monomer component contains: an acrylic monomer (X) containing, within one molecule, two aromatic rings and two acryloyloxy groups, and having a Mw of from 400 to 580; and at least one of: a (meth)acrylic monomer (A) containing, within one molecule, one or more ether bonds and two (meth)acryloyloxy groups, and having a Mw of from 200 to 400; a (meth)acrylic monomer (B) not containing, within one molecule, a ring structure other than an aromatic ring and one (meth)acryloyloxy group, and having a Mw of from 130 to 240; or a (meth)acrylic monomer (C) containing, within one molecule, a hydrocarbon skeleton and two (meth) acryloyloxy groups, and having a Mw of from 190 to 280.

20 Claims, No Drawings

PHOTOCURABLE COMPOSITION, DENTURE BASE, AND PLATE DENTURE

TECHNICAL FIELD

The present invention relates to a photocurable composition, a denture base, and a plate denture.

BACKGROUND ART

Conventionally, a denture base made of resin (referred to as "resin base") has been produced by a method in which a plaster mold adapted to an intraoral shape of a patient is first produced by a dental method, and then a curable resin is poured into the plaster mold, followed by curing the curable resin.

In recent years, a method has been proposed in which the intraoral shape of a patient is measured by a three-dimensional measurement and a denture base is produced based on the measured result, instead of the above described method utilizing a plaster mold, so as to reduce the number of hospital visits of patients and to allow for an efficient production of a denture base (see, for example, the following Patent Document 1). Further, a method is disclosed in which a dental prosthesis is produced using a 3D printer (see, for example, the following Patent Document 2).

RELATED ART DOCUMENTS

Patent Documents

Patent Document 1: Japanese Patent Application Laid-Open (JP-A) No. 6-78937
Patent Document 2: Japanese Patent (JP-B) No. 4160311

SUMMARY OF THE INVENTION

Technical Problem

One example of the method of producing a dental prosthesis, a medical device for intraoral use, or a tooth and/or jaw model (hereinafter, collectively referred to as "dental prosthesis or the like") using a 3D printer is a method referred to as "stereolithography", in which a dental prosthesis is produced by forming a photocurable composition into the shape of the dental prosthesis or the like, and then the resulting shaped product is subjected to photocuring.

In a case in which a dental prosthesis or the like (a denture base, in particular) is produced by stereolithography, it is required that the photocurable composition after being subjected to photocuring has an excellent flexural strength and flexural modulus, in view of practical use of the dental prosthesis or the like. Further, in this case, the photocurable composition after photocuring is also required to have an excellent Charpy impact strength, in view of durability of the dental prosthesis or the like.

An object of an embodiment according to the invention is to provide a photocurable composition which is used for the production by stereolithography of a dental prosthesis, a medical device for intraoral use, or a tooth and/or jaw model, and which has an excellent flexural strength, flexural modulus, and Charpy impact strength after being subjected to photocuring.

Another object of the embodiment according to the invention is to provide: a denture base which is produced using the above described photocurable composition, and which has an excellent flexural strength, flexural modulus, and Charpy impact strength; and a plate denture including the denture base.

Solution to Problem

The present inventors have found out, as a result of intensive studies, that a photocurable composition containing a combination of specific monomer species has an excellent flexural strength, flexural modulus, and Charpy impact strength after being subjected to photocuring, and that the photocurable composition is particularly suitable for the production by stereolithography of a dental prosthesis or the like (in other words, a dental prosthesis, a medical device for intraoral use, or a tooth and/or jaw model), thereby completing the present invention. In other words, specific means for solving the above described problems are as follows.

<1> A photocurable composition that is used for production by stereolithography of a dental prosthesis, a medical device for intraoral use, or a tooth and/or jaw model, the photocurable composition comprising:

a (meth)acrylic monomer component and a photopolymerization initiator;

wherein the (meth)acrylic monomer component comprises:

an acrylic monomer (X) that is at least one selected from diacrylic monomers containing, within one molecule, two aromatic rings and two acryloyloxy groups, and that has a weight average molecular weight of from 400 to 580; and at least one selected from the group consisting of:

a (meth)acrylic monomer (A) that is at least one selected from di(meth)acrylic monomers not containing, within one molecule, an aromatic ring and containing, within one molecule, one or more ether bonds and two (meth)acryloyloxy groups, and that has a weight average molecular weight of from 200 to 400;

a (meth)acrylic monomer (B) that is at least one selected from (meth)acrylic monomers not containing, within one molecule, an aromatic ring and containing, within one molecule, a ring structure other than an aromatic ring and one (meth)acryloyloxy group, and that has a weight average molecular weight of from 130 to 240; and a (meth)acrylic monomer (C) that is at least one selected from di(meth)acrylic monomers not containing, within one molecule, an aromatic ring or an ether bond and containing, within one molecule, a hydrocarbon skeleton and two (meth)acryloyloxy groups, and that has a weight average molecular weight of from 190 to 280.

<2> The photocurable composition according to <1>, wherein at least one of the diacrylic monomers constituting the acrylic monomer (X) contains an ether bond within one molecule.

<3> The photocurable composition according to <1> or <2>, wherein at least one of the diacrylic monomers constituting the acrylic monomer (X) contains from one to four ether bonds within one molecule.

<4> The photocurable composition according to any one of <1> to <3>, wherein at least one of the diacrylic monomers constituting the acrylic monomer (X) is a compound represented by the following Formula (x-1):

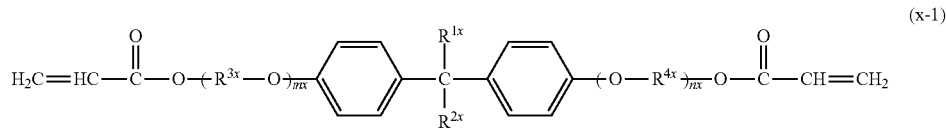
(x-1)

wherein, in Formula (x-1), each of $R^{1x}$ and $R^{2x}$ independently represents a hydrogen atom or a methyl group; each of $R^{3x}$ and $R^{4x}$ independently represents a straight chain or branched chain alkylene group having from 2 to 4 carbon atoms; and each of mx and nx independently represents a number from 0 to 4, and wherein mx and nx satisfy: $1 \leq (mx+nx) \leq 4$.

<5> The photocurable composition according to any one of <1> to <4>, wherein at least one of the diacrylic monomers constituting the acrylic monomer (X) is a compound represented by the following Formula (x-2):

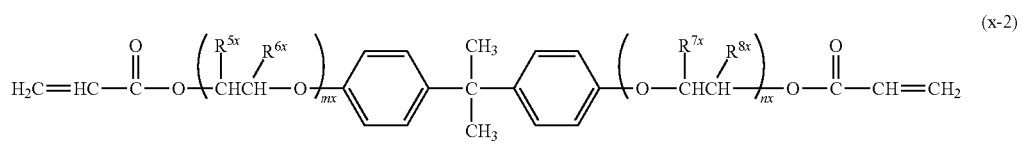
(x-2)

wherein, in Formula (x-2), each of $R^{5x}$, $R^{6x}$, $R^{7x}$, and $R^{8x}$ independently represents a hydrogen atom or a methyl group; and each of mx and nx independently represents a number from 0 to 4, and wherein mx and nx satisfy: $1 \leq (mx+nx) \leq 4$.

<6> The photocurable composition according to any one of <1> to <5>, wherein at least one of the di(meth)acrylic monomers constituting the (meth)acrylic monomer (A) is a compound represented by the following Formula (a-1):

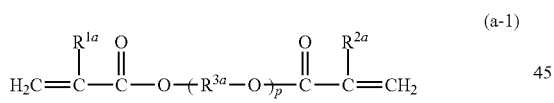
(a-1)

wherein, in Formula (a-1), each of $R^{1a}$ and $R^{2a}$ independently represents a hydrogen atom or a methyl group; each $R^{3a}$ independently represents a straight chain or branched chain alkylene group having from 2 to 4 carbon atoms; and p represents a number from 2 to 4.

<7> The photocurable composition according to any one of <1> to <6>, wherein at least one of the di(meth)acrylic monomers constituting the (meth)acrylic monomer (A) is a compound represented by the following Formula (a-2):

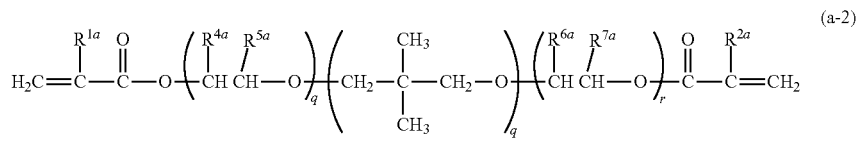
(a-2)

wherein, in Formula (a-2), each of $R^{1a}$, $R^{2a}$, $R^{4a}$, $R^{5a}$, $R^{6a}$, and $R^{7a}$ independently represents a hydrogen atom or a methyl group; and each of p, q, and r independently represents 0 or 1, and wherein p, q, and r satisfy: p+q+r≥2.

<8> The photocurable composition according to any one of <1> to <7>, wherein at least one of the (meth)acrylic monomers constituting the (meth)acrylic monomer (B) is a compound represented by the following Formula (b-1):

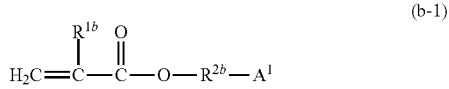

(b-1)

wherein, in Formula (b-1), $R^{1b}$ represents a hydrogen atom or a methyl group; $R^{2b}$ represents a single bond or a methylene group; and $A^1$ represents a ring structure other than an aromatic ring.

<9> The photocurable composition according to any one of <1> to <8>, wherein at least one of the (meth)acrylic monomers constituting the (meth)acrylic monomer (B) is a compound represented by the following Formula (b-2):

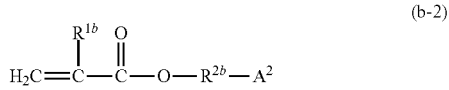

(b-2)

wherein, in Formula (b-2), $R^{1b}$ represents a hydrogen atom or a methyl group; $R^{2b}$ represents a single bond or a methylene group; and $A^2$ represents a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton.

<10> The photocurable composition according to any one of <1> to <9>, wherein at least one of the di(meth)acrylic monomers constituting the (meth)acrylic monomer (C) is a compound represented by the following Formula (c-1):

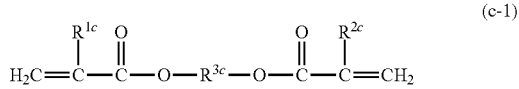

(c-1)

wherein, in Formula (c-1), each of $R^{1c}$ and $R^{2c}$ independently represents a hydrogen atom or a methyl group; and $R^{3c}$ represents an alkylene group having from 1 to 9 carbon atoms.

<11> The photocurable composition according to any one of <1> to <10>, wherein at least one of the di(meth)acrylic monomers constituting the (meth)acrylic monomer (C) is a compound represented by the following Formula (c-2):

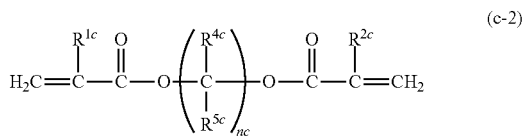

(c-2)

wherein, in Formula (c-2), each of $R^{1c}$ and $R^{2c}$ independently represents a hydrogen atom or a methyl group; each of $R^{4c}$ and $R^{5c}$ independently represents a hydrogen atom or a methyl group; and nc represents a number from 1 to 9, and wherein an alkylene group represented by —$(CR^{4c}R^{5c})_{nc}$— has from 1 to 9 carbon atoms.

<12> The photocurable composition according to any one of <1> to <11>, wherein the photopolymerization initiator is at least one selected from alkylphenone compounds or acylphosphine oxide compounds.

<13> The photocurable composition according to any one of <1> to <12>, wherein a content of the acrylic monomer (X) is from 550 parts by mass to 800 parts by mass with respect to 1,000 parts by mass of a total content of the (meth)acrylic monomer component.

<14> The photocurable composition according to any one of <1> to <13>, wherein a content of the (meth)acrylic monomer (A) is from 100 parts by mass to 450 parts by mass with respect to 1,000 parts by mass of a total content of the (meth)acrylic monomer component.

<15> The photocurable composition according to any one of <1> to <14>, wherein a content of the (meth)acrylic monomer (B) is from 100 parts by mass to 450 parts by mass with respect to 1,000 parts by mass of a total content of the (meth)acrylic monomer component.

<16> The photocurable composition according to any one of <1> to <15>, wherein a content of the (meth)acrylic monomer (C) is from 100 parts by mass to 450 parts by mass with respect to 1,000 parts by mass of a total content of the (meth)acrylic monomer component.

<17> The photocurable composition according to any one of <1> to <16>, wherein a content of the photopolymerization initiator is from 1 part by mass to 50 parts by mass with respect to 1,000 parts by mass of a total content of the (meth)acrylic monomer component.

<18> The photocurable composition according to any one of <1> to <17>, wherein the photocurable composition has a viscosity, as measured using a Type E viscometer at 25° C. and 50 rpm, of from 20 mPa·s to 1500 mPa·s.

<19> The photocurable composition according to any one of <1> to <18>, which is used for the production by stereolithography of a denture base or a mouthpiece.

<20> The photocurable composition according to any one of <1> to <19>, which is used for the production by stereolithography of a denture base.

<21> A denture base that is a cured product of the photocurable composition according to <20>.

<22> A plate denture comprising the denture base according to <21> and an artificial tooth fixed to the denture base.

Advantageous Effects of Invention

The embodiment according to the invention provides a photocurable composition which is used for the production by stereolithography of a dental prosthesis, a medical device for intraoral use, or a tooth and/or jaw model, and which has an excellent flexural strength, flexural modulus, and Charpy impact strength, after being subjected to photocuring.

Further, the embodiment according to the invention provides: a denture base which is produced by stereolithography, using the above described photocurable composition, and which has an excellent flexural strength, flexural modulus, and Charpy impact strength; and a plate denture including the denture base.

DESCRIPTION OF EMBODIMENTS

An embodiment according to the invention (hereinafter, also referred to as "present embodiment") are now described. In the present specification, any numerical range indicated using an expression "from * to" represents a range in which numerical values described before and after the "to" are included in the range as a lower limit value and an upper limit value. In the present specification, the term "ether bond" refers to a bond (a bond represented by —O—) in which two hydrocarbon groups are bound via an oxygen atom, as is commonly defined. Accordingly, "—O—" in an ester bond (—C(=O)—O—) is not included in the definition of the "ether bond". Further, in the present specification, the term "(meth)acrylate" refers to an acrylate or a methacrylate, and the term "(meth)acryloyloxy group" refers to an acryloyloxy group or a methacryloyloxy group.

[Photocurable Composition]

The photocurable composition according to the present embodiment is:

a photocurable composition which is used for the production by stereolithography of a dental prosthesis, a medical device for intraoral use, or a tooth and/or jaw model, wherein the photocurable composition comprises a (meth)acrylic monomer component and a photopolymerization initiator; and wherein the (meth)acrylic monomer component comprises:

an acrylic monomer (X) which is at least one selected from diacrylic monomers containing, within one molecule, two aromatic rings and two acryloyloxy groups, and which has a weight average molecular weight of from 400 to 580; and at least one selected from the group consisting of:

a (meth)acrylic monomer (A) which is at least one selected from di(meth)acrylic monomers not containing an aromatic ring and containing, within one molecule, one or more ether bonds and two (meth)acryloyloxy groups within one molecule, and which has a weight average molecular weight of from 200 to 400;

a (meth)acrylic monomer (B) which is at least one selected from (meth)acrylic monomers not containing, within one molecule, an aromatic ring and containing, within one molecule, a ring structure other than an aromatic ring and one (meth)acryloyloxy group, and which has a weight average molecular weight of from 130 to 240; and a (meth)acrylic monomer (C) which is at least one selected from di(meth)acrylic monomers not containing, within one molecule, anaromatic ring or an ether bond and containing, within one molecule, a hydrocarbon skeleton and two (meth)acryloyloxy groups, and which has a weight average molecular weight of from 190 to 280.

The photocurable composition according to the present embodiment has an excellent flexural strength, flexural modulus, and Charpy impact strength, after being subjected to photocuring, by including a combination of: the acrylic monomer (X); and at least one selected from the group consisting of the (meth)acrylic monomer (A), the (meth)acrylic monomer (B), and the (meth)acrylic monomer (C) (hereinafter, also referred to as "at least one of the (meth)acrylic monomers (A) to (C)").

Accordingly, a dental prosthesis or the like (a denture base, in particular) which is produced by stereolithography, using the photocurable composition according to the present embodiment, also has an excellent flexural strength, flexural modulus, and Charpy impact strength.

Further, the photocurable composition according to the present embodiment has a viscosity suitable for the production by stereolithography of a dental prosthesis or the like.

In the present embodiment, the "(meth)acrylic monomer component" refers to entire (meth)acrylic monomers included in the photocurable composition according to the present embodiment.

The "(meth)acrylic monomer component" includes, at least: the acrylic monomer (X); and at least one of the (meth)acrylic monomers (A) to (C).

The "(meth)acrylic monomer component" may include another (meth)acrylic monomer, other than the acrylic monomer (X) and the (meth)acrylic monomers (A) to (C), if necessary.

The photocurable composition according to the present embodiment encompasses the following first to third embodiments.

The first embodiment is an embodiment in which the (meth)acrylic monomer component in the present embodiment includes at least the acrylic monomer (X) and the (meth)acrylic monomer (A).

The second embodiment is an embodiment in which the (meth)acrylic monomer component in the present embodiment includes at least the acrylic monomer (X) and the (meth)acrylic monomer (B).

The third embodiment is an embodiment in which the (meth)acrylic monomer component in the present embodiment includes at least the acrylic monomer (X) and the (meth)acrylic monomer (C).

At least two of the scope of the first embodiment, the scope of the second embodiment, or the scope of the third embodiment may have some components in common. For example, an embodiment in which the (meth)acrylic monomer component includes the acrylic monomer (X), the (meth)acrylic monomer (A), the (meth)acrylic monomer (B), and the (meth)acrylic monomer (C) falls within the scope of any of the first to third embodiments.

In the photocurable composition according to the present embodiment (in other words, the first to third embodiments of the present embodiment; the same shall apply hereinafter), the Charpy impact strength after photocuring is improved due to incorporation of the acrylic monomer (X), as compared to the case in which a dimethacrylic monomer containing two aromatic rings and two methacryloyloxy groups within one molecule is included, instead of the acrylic monomer (X).

In the photocurable composition according to the present embodiment, the flexural strength and the flexural modulus after photocuring are improved due to the incorporation of the acrylic monomer (X), as compared to the case in which an acrylic monomer containing one aromatic ring and one acryloyloxy group within one molecule is included, instead of the acrylic monomer (X).

In the photocurable composition according to the present embodiment, the incorporation of the acrylic monomer (X) allows for inhibiting a phenomenon in which a crystallinity of the monomers is increased excessively, as compared to the case in which a diacrylic monomer containing one aromatic ring and two acryloyloxy groups within one molecule is included, instead of the acrylic monomer (X). As a result, the viscosity of the photocurable composition is reduced.

In the photocurable composition according to the present embodiment, the viscosity of the photocurable composition is reduced due to the incorporation of the acrylic monomer (X), as compared to the case in which an acrylic monomer containing three or more aromatic rings within one molecule is used, instead of the acrylic monomer (X).

In the photocurable composition according to the present embodiment, the Charpy impact strength after photocuring is improved due to the incorporation of the acrylic monomer (X), as compared to the case in which an acrylic monomer containing three or more acryloyloxy groups within one molecule is used, instead of the acrylic monomer (X).

Further, in the photocurable composition according to the present embodiment, the flexural strength and the flexural modulus after photocuring are improved due to the incorporation of the acrylic monomer (X), as compared to the case of using, instead of the acrylic monomer (X), an acrylic monomer which is at least one selected from diacrylic monomers containing two aromatic rings and two acryloyloxy groups within one molecule, and which has a weight average molecular weight of greater than 580.

Note that the lower limit of the weight average molecular weight of the acrylic monomer (X), which is 400, is a lower limit defined in view of ease of production or ease of availability of the monomer.

In addition, in the photocurable composition according to the present embodiment, the flexural strength and the flexural modulus after photocuring are further improved, due to the incorporation of at least one of the (meth)acrylic monomers (A) to (C), in addition to the acrylic monomer (X).

More specifically, the photocurable composition according to the first embodiment of the present embodiment is, as described above, a photocurable composition in which the (meth)acrylic monomer component includes at least the acrylic monomer (X) and the (meth)acrylic monomer (A).

As described above, the (meth)acrylic monomer (A) is a (meth)acrylic monomer which is at least one selected from di(meth)acrylic monomers not containing, within one molecule, an aromatic ring and containing, within one molecule, one or more ether bonds and two (meth)acryloyloxy groups, and which has a weight average molecular weight of from 200 to 400.

According to the photocurable composition of the first embodiment, the flexural strength and the flexural modulus of the composition after photocuring are improved, as compared to those of a photocurable composition which includes, instead of the (meth)acrylic monomer (A) in the first embodiment, a (meth)acrylic monomer not containing an aromatic ring and containing one or more ether bonds and two (meth)acryloyloxy groups within one molecule, and having a weight average molecular weight of greater than 400, and which composition does not fall within the scope of any of the first to third embodiments.

Note that the lower limit of the weight average molecular weight of the (meth)acrylic monomer (A), which is 200, is a lower limit defined in view of the ease of production or ease of availability of the monomer.

The photocurable composition according to the second embodiment of the present embodiment is, as described above, a photocurable composition in which the (meth)acrylic monomer component includes at least the acrylic monomer (X) and the (meth)acrylic monomer (B). As described above, the (meth)acrylic monomer (B) is a (meth)acrylic monomer which is at least one selected from (meth)acrylic monomers not containing, within one molecule, an aromatic ring and containing, within one molecule, a ring structure other than an aromatic ring and one (meth)acryloyloxy group, and which has a weight average molecular weight of from 130 to 240.

According to the photocurable composition of the second embodiment, the flexural strength and the flexural modulus of the composition after photocuring are improved, as compared to those of a photocurable composition which includes, instead of the (meth)acrylic monomer (B) in the second embodiment, a (meth)acrylic monomer containing a ring structure other than an aromatic ring and one (meth)acryloyloxy group within one molecule, and having a weight average molecular weight of greater than 240, and which composition does not fall within the scope of any of the first to third embodiments.

Further, according to the photocurable composition of the second embodiment, the flexural strength and the flexural modulus of the composition after photocuring are improved, as compared to those of a photocurable composition which includes, instead of the (meth)acrylic monomer (B) in the second embodiment, a (meth)acrylic monomer containing no ring structure within one molecule, and which composition does not fall within the scope of any of the first to third embodiments.

Note that the lower limit of the weight average molecular weight of the (meth)acrylic monomer (B), which is 130, is a lower limit defined in view of the ease of production or ease of availability of the monomer.

The photocurable composition according to the third embodiment of the present embodiment is, as described above, a photocurable composition in which the (meth)acrylic monomer component includes at least the acrylic monomer (X) and the (meth)acrylic monomer (C).

As described above, the (meth)acrylic monomer (C) is a (meth)acrylic monomer which is at least one selected from di(meth)acrylic monomers not containing, within one molecule, an aromatic ring nor ether bond and containing, within one molecule, a hydrocarbon skeleton and two (meth)acryloyloxy groups, and which has a weight average molecular weight of from 190 to 280.

According to the photocurable composition of the third embodiment, the flexural strength and the flexural modulus of the composition after photocuring are improved, as compared to those of a photocurable composition which includes, instead of the (meth)acrylic monomer (C) in the third embodiment, a (meth)acrylic monomer not containing, within one molecule, an aromatic ring nor ether bond and containing, within one molecule, a hydrocarbon skeleton and two (meth)acryloyloxy groups, and having a weight average molecular weight of greater than 280, and which composition does not fall within the scope of any of the first to third embodiments.

Note that the lower limit of the weight average molecular weight of the (meth)acrylic monomer (C), which is 190, is a lower limit defined in view of the ease of production or ease of availability of the monomer.

The photocurable composition according to the present embodiment preferably satisfies the following flexural strength and the following flexural modulus, after being subjected to photocuring, in terms of the practical use of the resulting dental prosthesis or the like (the resulting denture base, in particular).

In other words, the photocurable composition according to the present embodiment preferably satisfies a flexural strength, as measured below, of 60 MPa or more, and more preferably, 65 MPa or more. Specifically, the measurement of the flexural strength is carried out as follows. The photocurable composition is formed into a shaped product having a size of 64 mm×10 mm×3.3 mm thickness, and the resulting formed product is subjected to UV light irradiation at 5 J/cm$^2$ to carry out photocuring, thereby obtaining a stereolithographed product (namely, a cured product; the same shall apply hereinafter). The resulting stereolithographed product is stored in a constant temperature water bath controlled at 37±1° C. for 50±2 hours, and the flexural strength of the stereolithographed product after storage is measured in accordance with ISO 20795-1: 2008 (or JIS T 6501: 2012).

Further, the photocurable composition according to the present embodiment preferably satisfies a flexural modulus, as measured below, of 1,500 MPa or more, and more preferably, 2,000 MPa or more. Specifically, the measurement of the flexural modulus is carried out as follows. The photocurable composition is formed into a shaped product having a size of 64 mm×10 mm×3.3 mm thickness, and the resulting shaped product is subjected to UV light irradiation at 5 J/cm$^2$ to carry out photocuring, thereby obtaining a stereolithographed product. The resulting stereolithographed product is stored in a constant temperature water bath controlled at 37±1° C. for 50±2 hours, and the flexural modulus of the stereolithographed product after storage is measured in accordance with ISO 20795-1: 2008 (or JIS T 6501: 2012).

In addition, the photocurable composition according to the present embodiment preferably satisfies the following Charpy impact strength, in terms of the durability of the resulting dental prosthesis or the like (the resulting denture base, in particular).

In other words, the photocurable composition according to the present embodiment preferably satisfies a Charpy impact strength, as measured below, of 1.0 kJ/m$^2$ or more. Specifically, the measurement of the Charpy impact strength is carried out as follows. The photocurable composition is formed into a shaped product having a size of 80 mm×10 mm×4 mm thickness, and the resulting formed product is subjected to UV light irradiation at 5 J/cm$^2$ to carry out photocuring, thereby obtaining a stereolithographed product. The resulting stereolithographed product is stored in a constant temperature water bath controlled at 37±1° C. for 50±2 hours. Then, a notch in the shape of a letter A and having a depth of 2 mm is provided at the central portion in a longitudinal direction of the stereolithographed product after storage, to obtain a test specimen with a single-notch. The Charpy impact strength of the resulting test specimen with a single-notch is measured in accordance with ISO 179-1: 2010 (or JIS K 7111-1: 2012), and under conditions of a hammer energy of 0.5 J, a swing angle of 148 degrees, a test temperature of 23° C., and edgewise impact.

The photocurable composition according to the present embodiment is used for the production by stereolithography of a dental prosthesis or the like (namely, a dental prosthesis, a medical device for intraoral use, or a tooth and/or jaw model).

In the present embodiment, the dental prosthesis may be, for example, a denture base, a denture, an inlay, a crown, a bridge, a temporary crown, or a temporary bridge. Among these, a denture base is preferred.

Further, in the present embodiment, the medical device for intraoral use may be, for example, an orthodontic appliance (such as a mouthpiece, or an orthodontic appliance), a bite splint, a tray for obtaining an impression, or a guide for use in surgery. Among these, an orthodontic appliance is preferred, and a mouthpiece is more preferred.

The dental prosthesis or the like (namely, a dental prosthesis, medical device for intraoral use, or a tooth and/or jaw model) is preferably a dental prosthesis or an orthodontic appliance, more preferably a denture base or a mouthpiece, and particularly preferably a denture base.

In the present embodiment, the term "stereolithography" refers to one of the three-dimensional shaping methods utilizing a 3D printer.

Examples of stereolithography methods include an SLA (Stereo Lithography Apparatus) method, a DLP (Digital Light Processing) method, and an ink-jet method.

The photocurable composition according to the present embodiment is particularly suitable for a SLA or a DLP stereolithography method.

Examples of the SLA method include a method in which a spot-shaped UV laser beam is irradiated to a photocurable composition to obtain a three-dimensional shaped product.

In a case in which a dental prosthesis or the like is produced by the SLA method, the production thereof may be carried out, for example, as follows. Specifically, the photocurable composition according to the present embodiment is pooled in a container, and a spot-like UV laser beam is selectively irradiated to a liquid surface of the photocurable composition so as to obtain a desired pattern. In this manner, the photocurable composition is cured to form a cured layer having a desired thickness on a shaping table. Subsequently, the shaping table is lowered, so that the photocurable composition in a liquid state is supplied over the cured layer, in an amount sufficient for forming one layer, and the curing is carried out in the same manner as described above. This operation is repeated to obtain cured layers disposed one on another in layers. In this manner, a dental prosthesis or the like can be produced.

Examples of the DLP method include a method in which planar light is irradiated to a photocurable composition to obtain a three-dimensional shaped product.

As to the method of obtaining a three-dimensional shaped product by the DLP method, for example, the description in JP-B 5111880 and JP-B 5235056 can be referred to, if appropriate.

In a case in which a dental prosthesis or the like is produced by the DLP method, the production thereof may be carried out, for example, as follows. Specifically, a lamp which emits light other than a laser beam, such as a high pressure mercury lamp, an ultra-high pressure mercury lamp, or a low pressure mercury lamp, or alternatively, an LED is used as a light source. A planar drawing mask in which a plurality of digital micro mirror shutters are disposed planarly, is disposed between the light source and the surface of the photocurable composition to be shaped. Then light is irradiated to the surface of the photocurable composition to be shaped through the planar drawing mask, to form a cured layer having a predetermined pattern shape. This operation is repeated so that cured layers are formed and layered one on another, sequentially. In this manner, a dental prosthesis or the like can be produced.

Examples of the ink-jet method include a method in which droplets of a photocurable composition is continuously discharged onto a substrate through an ink-jet nozzle, and then light is irradiated to the droplets adhered to the substrate to obtain a three-dimensional shaped product.

In a case in which a dental prosthesis or the like is produced by an ink-jet method, the production thereof may be carried out, for example, as follows. Specifically, while scanning a plane with a head including an ink-jet nozzle and a light source, the photocurable composition is discharged onto a substrate through the ink-jet nozzle. At the same time, light is irradiated to the discharged photocurable composition to form a cured layer. This operation is repeated so that cured layers are formed and layered one on another, sequentially. In this manner, a dental prosthesis or the like can be produced.

The photocurable composition according to the present embodiment preferably has a viscosity at 25° C. and at 50 rpm, as measured using a Type E viscometer, of from 20 mPa·s to 1,500 mPa·s, in terms of suitability for the production by stereolithography of a dental prosthesis or the like. The lower limit of the viscosity is more preferably 50 mPa·s. The upper limit of the viscosity is more preferably 1,000 mPa·s, and still more preferably 500 mPa·s.

The viscosity at 25° C. and at 50 rpm of the photocurable composition according to the present embodiment may be adjusted depending on the method of the stereolithography to be used.

In a case in which a dental prosthesis or the like is produced by the SLA method, for example, the viscosity of the photocurable composition is preferably from 50 mPa·s to 1500 mPa·s, and more preferably from 50 mPa·s to 1000 mPa·s.

In a case in which a dental prosthesis or the like is produced by the DLP method, for example, the viscosity of the photocurable composition is preferably from 50 mPa·s to 500 mPa·s, and more preferably from 50 mPa·s to 250 mPa·s.

In a case in which a dental prosthesis or the like is produced by the ink-jet method, for example, the viscosity of the photocurable composition is preferably from 20 mPa·s to 500 mPa·s, and more preferably from 20 mPa·s to 100 mPa·s.

Components of the photocurable composition according to the present embodiment (namely, the first to third embodiments) will now be described.

<Acrylic Monomer (X)>

The (meth)acrylic monomer component in the present embodiment includes the acrylic monomer (X) which is at least one selected from diacrylic monomers containing, within one molecule, two aromatic rings and two acryloyloxy groups, and which has a weight average molecular weight of from 400 to 580.

The acrylic monomer (X) may consist of one type of diacrylic monomer containing, within one molecule, two aromatic rings and two acryloyloxy groups, or may be a mixture composed of two or more types of the diacrylic monomers.

It is preferable that at least one of the diacrylic monomers constituting the acrylic monomer (X) contains an ether bond within one molecule, in terms of further improving the Charpy impact strength after photocuring. Specifically, when at least one of the diacrylic monomers constituting the acrylic monomer (X) contains an ether bond within one molecule, the degree of freedom of molecular motion is increased to impart flexibility to the cured product after photocuring, thereby improving its toughness. As a result, the Charpy impact strength of the cured product (namely, the Charpy impact strength of the photocurable composition after photocuring) is improved.

It is more preferable that at least one of the diacrylic monomers contains from one to four ether bonds within one molecule.

When the number of ether bonds within one molecule, in at least one of the diacrylic monomers, is four or less, the flexural strength and the flexural modulus after photocuring are further improved.

The number of ether bonds within one molecule is still more preferably from two to four, and particularly preferably from two to three, in terms of further improving the flexural strength and the flexural modulus after photocuring.

It is still more preferable that at least one of the diacrylic monomers is a compound represented by the following Formula (x-1), in terms of reducing the viscosity of the photocurable composition, and further improving the Charpy impact strength, the flexural strength, and the flexural modulus, after photocuring.

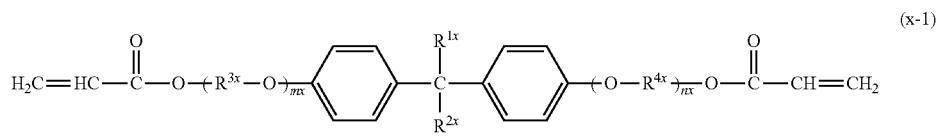

In Formula (x-1), each of $R^{1x}$ and $R^{2x}$ independently represents a hydrogen atom or a methyl group; each of $R^{3x}$ and $R^{4x}$ independently represents a straight chain or branched chain alkylene group having from 2 to 4 carbon atoms; and each of mx and nx independently represents a number from 0 to 4, with the proviso that mx and nx satisfy the relation: $1 \leq (mx+nx) \leq 4$.].

In a case in which a plurality of $R^{3x}$s are present in the compound represented by Formula (x-1), the plurality of $R^{3x}$s may be the same as or different from each other. The same applies for $R^{4x}$.

In Formula (x-1), each of $R^{1x}$ and $R^{2x}$ is preferably a methyl group.

Further, it is preferable that each of $R^{3x}$ and $R^{4x}$ independently represents an ethylene group, a trimethylene group, a tetramethylene group, a 1-methylethylene group, a 1-ethylethylene group or a 2-methyltrimethylene group, and more preferably, an ethylene group or a 1-methylethylene group.

In addition, it is preferable that both of $R^{3x}$ and $R^{4x}$ are ethylene groups, trimethylene groups, tetramethylene groups, 1-methylethylene groups, or 2-methyltrimethylene groups, and more preferably both are ethylene groups or 1-methylethylene groups.

Although mx+nx is from 1 to 4, it is particularly preferable that mx+nx is from 2 to 3, in terms of further improving the flexural strength and the flexural modulus after photocuring.

It is still more preferable that at least one of the diacrylic monomers constituting the acrylic monomer (X) is a compound represented by the following Formula (x-2), in terms of reducing the viscosity of the photocurable composition, and further improving the Charpy impact strength, the flexural strength, and the flexural modulus, after photocuring.

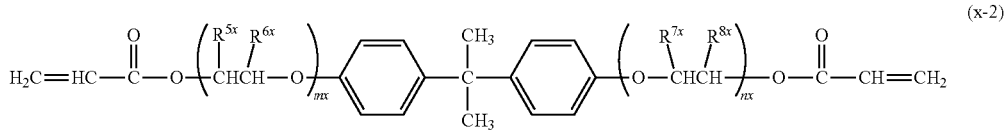

In Formula (x-2), each of $R^{5x}$, $R^{6x}$, $R^{7x}$, and $R^{8x}$ independently represents a hydrogen atom or a methyl group; and each of mx and nx independently represents a number from 0 to 4, with the proviso that mx and nx satisfy the relation: $1 \leq (mx+nx) \leq 4$.

In a case in which a plurality of $R^{5x}$s are present in the compound represented by Formula (x-2), the plurality of $R^{5x}$s may be the same as or different from each other. The same applies for each of $R^{6x}$, $R^{7x}$, and $R^{8x}$.

In Formula (x-2), it is preferable that one of $R^{5x}$ or $R^{6x}$ is a methyl group, and the other is a hydrogen atom. At the same time, it is preferable that one of $R^{7x}$ or $R^{8x}$ is a methyl group and the other is a hydrogen atom.

In Formula (x-2), it is particularly preferable that $R^{5x}$ and $R^{8x}$ are both methyl groups, and $R^{6x}$ and $R^{7x}$ are both hydrogen atoms.

Although mx+nx is from 1 to 4, it is preferable that mx+nx is from 2 to 3, in terms of further improving the flexural strength and the flexural modulus after photocuring.

Specific examples of the acrylic monomer (X) include: ethoxylated bisphenol A diacrylates (EO=2 mol, 2.2 mol, 2.6 mol, 3 mol, and 4 mol), propoxylated bisphenol A diacrylates (PO=2 mol, 3 mol, and 4 mol), and ethoxylated bisphenol F diacrylates (EO=2 mol, 2.2 mol, 2.6 mol, 3 mol, and 4 mol).

In the photocurable composition according to the present embodiment, the content of the acrylic monomer (X) is preferably from 550 parts by mass to 800 parts by mass, more preferably from 600 parts by mass to 800 parts by mass, and still more preferably from 620 parts by mass to 800 parts by mass, with respect to 1,000 parts by mass of the total content of the (meth)acrylic monomer component.

<(Meth)Acrylic Monomer (A)>

The (meth)acrylic monomer component in the first embodiment of the present embodiment includes the (meth)acrylic monomer (A) which is at least one selected from di(meth)acrylic monomers not containing, within one molecule, an aromatic ring and containing, within one molecule, one or more ether bonds and two (meth)acryloyloxy groups, and which has a weight average molecular weight of from 200 to 400.

The (meth)acrylic monomer (A) may be included in the (meth)acrylic monomer component in the second embodiment and the (meth)acrylic monomer component in the third embodiment.

The (meth)acrylic monomer (A) may consist of one type of di(meth)acrylic monomer not containing, within one molecule, an aromatic ring and containing, within one molecule, one or more ether bonds and two (meth)acryloyloxy groups, or may be a mixture composed of two or more types of the di(meth)acrylic monomers.

It is preferable that at least one of the di(meth)acrylic monomers constituting the (meth)acrylic monomer (A) contains one or two ether bonds within one molecule, in terms of further improving the Charpy impact strength after photocuring.

It is preferable that at least one of the di(meth)acrylic monomers constituting the (meth)acrylic monomer (A) is a compound represented by the following Formula (a-1), in terms of further improving the Charpy impact strength after photocuring.

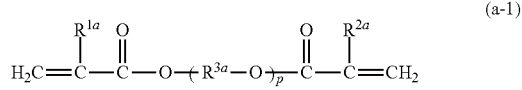

In Formula (a-1), each of $R^{1a}$ and $R^{2a}$ independently represents a hydrogen atom or a methyl group; each of $R^{3a}$s independently represents a straight chain or branched chain alkylene group having from 2 to 4 carbon atoms; and p represents a number from 2 to 4.

In Formula (a-1), a plurality of $R^{3a}$s may be the same as or different from each other.

In Formula (a-1), p is preferably 2 or 3.

In Formula (a-1), it is preferable that $R^{1a}$ and $R^{2a}$ are both hydrogen atoms or both methyl groups.

Further, it is preferable that each of $R^{3a}$s independently represents an ethylene group, a trimethylene group, a tetramethylene group, a 1-methylethylene group, a 1-ethylethylene group, a 2-methyltrimethylene group, or a 2,2-dimethyltrimethylene group, and more preferably an ethylene group, a 1-methylethylene group or a 2,2-dimethyltrimethylene group.

It is preferable that at least one of the di(meth)acrylic monomers constituting the (meth)acrylic monomer (A) is a compound represented by the following Formula (a-2).

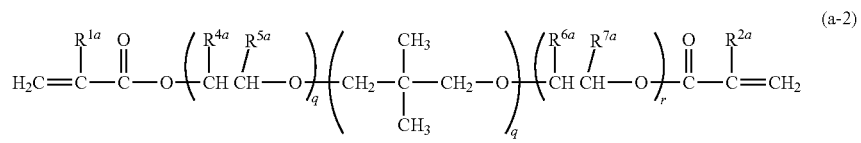

In Formula (a-2), each of $R^{1a}$, $R^{2a}$, $R^{4a}$, $R^{5a}$, $R^{6a}$ and $R^{7a}$ independently represents a hydrogen atom or a methyl group; and each of p, q and r independently represents 0 or 1, with the proviso that p, q and r satisfy the relation: $p+q+r \geq 2$.

In Formula (a-2), it is preferable that $R^{1a}$ and $R^{2a}$ are both hydrogen atoms or both methyl groups. It is preferable that $R^{4a}$ and $R^{7a}$ are both hydrogen atoms or both methyl groups, and $R^{5a}$ and $R^{6a}$ are both hydrogen atoms or both methyl groups.

Further, it is preferable that p and r are both 1.

The (meth)acrylic monomer (A) has a weight average molecular weight of from 200 to 400. The (meth)acrylic monomer (A) in the first embodiment preferably has a weight average molecular weight of from 200 to 350.

In a case in which the (meth)acrylic monomer component in the second embodiment or the third embodiment includes the (meth)acrylic monomer (A), the (meth)acrylic monomer (A) in the second embodiment or the third embodiment preferably has a weight average molecular weight of from 200 to 350, more preferably from 200 to 300, and particularly preferably from 200 to 250.

Examples of the (meth)acrylic monomer (A) include diethylene glycol di(meth)acrylate, triethylene glycol di(meth)acrylate, dipropylene glycol di(meth)acrylate, tripropylene glycol di(meth)acrylate, and propoxylated neopentyl glycol di(meth)acrylate.

In the photocurable composition according to the present embodiment, the content of the (meth)acrylic monomer (A) is preferably from 100 parts by mass to 450 parts by mass, more preferably from 100 parts by mass to 400 parts by mass, and particularly preferably from 120 parts by mass to 380 parts by mass, with respect to 1,000 parts by mass of the total content of the (meth)acrylic monomer component.

In a case in which the (meth)acrylic monomer component in the first embodiment includes at least one of the (meth)acrylic monomer (B) or (meth)acrylic monomer (C), the content of the (meth)acrylic monomer (A) is preferably 51% by mass or more, with respect to the total content of the (meth)acrylic monomer (A), (meth)acrylic monomer (B), and the (meth)acrylic monomer (C).

<(Meth)Acrylic Monomer (B)>

The (meth)acrylic monomer component in the second embodiment of the present embodiment includes the (meth)acrylic monomer (B) which is at least one selected from (meth)acrylic monomers not containing, within one molecule, an aromatic ring and containing, within one molecule, a ring structure other than an aromatic ring and one (meth)acryloyloxy group, and which has a weight average molecular weight of from 130 to 240.

The (meth)acrylic monomer (B) may be included in each of the (meth)acrylic monomer component in the first embodiment or the (meth)acrylic monomer component in the third embodiment.

The (meth)acrylic monomer (B) may consist of one type of (meth)acrylic monomer containing a ring structure other than an aromatic ring and one (meth)acryloyloxy group within one molecule, or may be a mixture composed of two or more types of the (meth)acrylic monomers.

In the (meth)acrylic monomer (B), the ring structure other than an aromatic ring is preferably an alicyclic structure or a heterocyclic structure.

The ring structure other than an aromatic ring is more preferably a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton. The ring structure containing a skeleton as described above may be substituted by a substituent such as an alkyl group (for example, a methyl group, an ethyl group, a propyl group, or a butyl group), or the like.

In the (meth)acrylic monomer (B), the ring structure other than an aromatic ring is preferably a polycyclic structure, and more preferably a ring structure containing a dicyclopentenyl skeleton, a dicyclopentanyl skeleton, an isobornyl skeleton, or a norbornyl skeleton, in terms of further improving the flexural strength and the flexural modulus after photocuring.

Further, at least one of the (meth)acrylic monomers constituting the (meth)acrylic monomer (B) is preferably a compound which does not contain an imide structure, in terms of reducing water absorption.

At least one of the (meth)acrylic monomers constituting the (meth)acrylic monomer (B) is preferably a compound represented by the following Formula (b-1).

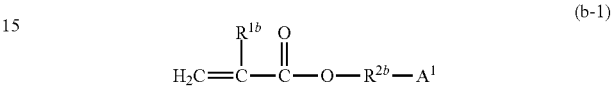

In Formula (b-1), $R^{1b}$ represents a hydrogen atom or a methyl group; $R^{2b}$ represents a single bond or a methylene group; and $A^1$ represents a ring structure other than an aromatic ring.

In Formula (b-1), preferred scope of the "ring structure other than an aromatic ring" represented by $A^1$ is as described above. In other words, it is more preferable that at least one of the (meth)acrylic monomers constituting the (meth)acrylic monomer (B) is a compound represented by the following Formula (b-2).

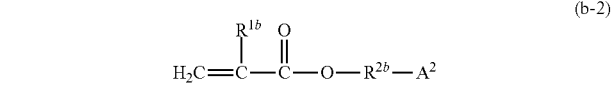

In Formula (b-2), $R^{1b}$ represents a hydrogen atom or a methyl group; $R^{2b}$ represents a single bond or a methylene group; and $A^2$ represents a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton or a dioxane skeleton.

The (meth)acrylic monomer (B) has a weight average molecular weight of from 130 to 240.

The (meth)acrylic monomer (B) in the second embodiment preferably has a weight average molecular weight of from 140 to 220.

In a case in which the (meth)acrylic monomer component in the first embodiment or the third embodiment includes the (meth)acrylic monomer (B), the (meth)acrylic monomer (B) in the first embodiment or the third embodiment preferably has a weight average molecular weight of from 150 to 240, and more preferably from 180 to 230.

Examples of the (meth)acrylic monomer (B) include isobornyl (meth)acrylate, norbornyl (meth)acrylate, dicyclopentenyl (meth)acrylate, dicyclopentanyl (meth)acrylate, cyclohexyl (meth)acrylate, tetrahydrofurfuryl (meth)acrylate, (meth)acryloylmorpholine, 4-tert-butylcyclohexanol (meth)acrylate, cyclohexanedimethanol di(meth)acrylate, (2-methyl-2-ethyl-1,3-dioxolane-4-yl) methyl acrylate, and cyclic trimethylolpropane formal acrylate.

In the photocurable composition according to the present embodiment, the content of the (meth)acrylic monomer (B) is preferably from 100 parts by mass to 450 parts by mass, more preferably from 130 parts by mass to 420 parts by mass, and particularly preferably from 150 parts by mass to 400 parts by mass, with respect to 1,000 parts by mass of the total content of the (meth)acrylic monomer component.

Further, in a case in which the (meth)acrylic monomer component in the second embodiment includes at least one of the above described (meth)acrylic monomer (A) or the (meth)acrylic monomer (C), content of the (meth)acrylic monomer (B) is preferably 51% by mass or more, with respect to the total content of the (meth)acrylic monomer (A), (meth)acrylic monomer (B), and the (meth)acrylic monomer (C).

<(Meth)Acrylic Monomer (C)>

The (meth)acrylic monomer component in the third embodiment of the present embodiment includes the (meth)acrylic monomer (C) which is at least one selected from di(meth)acrylic monomers not containing, within one molecule, an aromatic ring nor ether bond and containing, within one molecule, a hydrocarbon skeleton and two (meth)acryloyloxy groups, and which has a weight average molecular weight of from 190 to 280.

The (meth)acrylic monomer (C) may be included in each of the (meth)acrylic monomer component in the first embodiment or the (meth)acrylic monomer component in the second embodiment.

The (meth)acrylic monomer (C) may consist of one type of di(meth)acrylic monomer not containing, within one molecule, an aromatic ring nor ether bond and containing, within one molecule, a hydrocarbon skeleton and two (meth)acryloyloxy groups, or may be a mixture composed of two or more types of the di(meth)acrylic monomers.

It is preferable that at least one of the di(meth)acrylic monomers constituting the (meth)acrylic monomer (C) is a compound represented by the following Formula (c-1), in terms of further improving the flexural strength and the flexural modulus after photocuring.

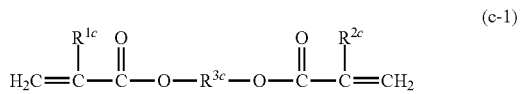
(c-1)

In Formula (c-1), each of $R^{1c}$ and $R^{2c}$ independently represents a hydrogen atom or a methyl group; and $R^{3c}$ represents an alkylene group having from 1 to 9 carbon atoms.

The alkylene group represented by $R^{3c}$ may be a straight chain alkylene group, or a branched chain alkylene group.

Further, it is more preferable that at least one of the di(meth)acrylic monomers constituting the (meth)acrylic monomer (C) is a compound represented by the following Formula (c-2), in terms of further improving the flexural strength and the flexural modulus after photocuring.

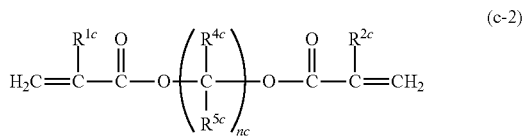
(c-2)

In Formula (c-2), each of $R^{1c}$ and $R^{2c}$ independently represents a hydrogen atom or a methyl group; each of $R^{4c}$ and $R^{5c}$ independently represents a hydrogen atom or a methyl group; and nc represents a number from 1 to 9, with the proviso that an alkylene group represented by $-(CR^{4c}R^{5c})_{nc}-$ has from 1 to 9 carbon atoms.

In a case in which a plurality of $R^{4c}$s are present in the compound represented by Formula (c-2), the plurality of $R^{4c}$s may be the same as or different from each other. The same applies for $R^{5c}$.

Specific examples of the (meth)acrylic monomer (C) include 1,3-butylene glycol diacrylate, neopentyl glycol diacrylate, 1,4-butanediol diacrylate, 1,4-butanediol dimethacrylate, 1,6-hexanediol diacrylate, 1,6-hexanediol dimethacrylate, 1,9-nonanediol diacrylate, ethylene glycol dimethacrylate, and 1,3-butylene glycol dimethacrylate.

In the photocurable composition according to the present embodiment, the content of the (meth)acrylic monomer (C) is preferably from 100 parts by mass to 450 parts by mass, more preferably from 100 parts by mass to 400 parts by mass, and particularly preferably from 100 parts by mass to 350 parts by mass, with respect to 1,000 parts by mass of the total content of the (meth)acrylic monomer component.

Further, in a case in which the (meth)acrylic monomer component in the third embodiment includes at least one of the above described (meth)acrylic monomer (A) or the (meth)acrylic monomer (B), the content of the (meth)acrylic monomer (C) is preferably 51% by mass or more, with respect to the total content of the (meth)acrylic monomer (A), (meth)acrylic monomer (B), and the (meth)acrylic monomer (C).

The (meth)acrylic monomer component may include another (meth)acrylic monomer other than the acrylic monomer (X), the (meth)acrylic monomer (A), the (meth)acrylic monomer (B), and the (meth)acrylic monomer (C).

Note, however, that the total content of the acrylic monomer (X), the (meth)acrylic monomer (A), the (meth)acrylic monomer (B), and the (meth)acrylic monomer (C) in the (meth)acrylic monomer component is preferably 60% by mass or more, more preferably 80% by mass or more, and still more preferably 90% by mass or more, with respect to the total amount of the (meth)acrylic monomer component.

<Photopolymerization Initiator>

The photocurable composition according to the present embodiment includes a photopolymerization initiator.

The photopolymerization initiator is not particularly limited as long as the photopolymerization initiator is capable of generating radicals when light is irradiated thereto. However, the photopolymerization initiator is preferably one which generates radicals by light irradiation at a wavelength used in the stereolithography.

In general, the wavelength of the light used in the stereolithography may be, for example, from 365 nm to 500 nm. However, the wavelength is preferably from 365 nm to 430 nm, and more preferably from 365 nm to 420 nm, in the view point of practical use.

Examples of the photopolymerization initiator which generates radicals by light irradiation at the wavelength used in the stereolithography include: alkylphenone compounds, acylphosphine oxide compounds, titanocene compounds, oxime ester compounds, benzoin compounds, acetophenone compounds, benzophenone compounds, thioxanthone compounds, α-acyloxime ester compounds, phenylglyoxylate compounds, benzyl compounds, azo compounds, diphenylsulfide compounds, organic pigment compounds, iron-phthalocyanine compounds, benzoin ether compounds, and anthraquinone compounds.

Among these, an alkylphenone compound and an acylphosphine oxide compound are preferred, in terms of reactivity and the like.

Examples of the alkylphenone compound include 1-hydroxy-cyclohexyl-phenyl-ketone (Irgacure 184: manufactured by BASF Japan Ltd.).

Examples of the acylphosphine oxide compound include bis(2,4,6-trimethylbenzoyl)-phenylphosphine oxide (Irgacure 819: manufactured by BASF Japan Ltd.), and 2,4,6-trimethylbenzoyl-diphenyl-phosphine oxide (Irgacure TPO: manufactured by BASF Japan Ltd.).

The photocurable composition according to the present embodiment may include only one type of the photopolymerization initiator, or two or more types of the photopolymerization initiators.

The content of the photopolymerization initiator (the total content, in a case in which two or more types thereof are included) in the photocurable composition according to the present embodiment is preferably from 1 part by mass to 50 parts by mass, more preferably from 2 parts by mass to 30 parts by mass, still more preferably from 3 parts by mass to 25 parts by mass, and particularly preferably from 3 parts by mass to 15 parts by mass, with respect to 1,000 parts by mass of the total content of the (meth)acrylic monomer component.

<Other Components>

The photocurable composition according to the present embodiment may include at least one other component other than the above mentioned components, if necessary.

Note, however, that the total content of the (meth)acrylic monomer component and the photopolymerization initiator is preferably from 60% by mass or more, more preferably from 80% by mass or more, and still more preferably from 90% by mass or more, with respect to the total amount of the photocurable composition.

Examples of the other components include coloring materials.

For example, in a case in which the photocurable composition according to the present embodiment is used for the production of a denture base, the photocurable composition may be colored to a color close to a gingival color by incorporating a coloring material, in terms of esthetics.

The coloring material is not limited as long as the coloring material does not interfere with the shaping of the photocurable composition by a 3D printer, and is less susceptible to discoloration. Examples thereof include pigments, dyes, and colorants. More specific examples of the coloring material include synthetic tar dyes, aluminum lakes of synthetic tar dyes, inorganic pigments, and natural pigments.

Further, examples of the other components also include other curable resins other than the above described (meth) acrylic monomer component (such as other curable monomers other than the above described (meth)acrylic monomer component).

In addition, examples of the other components also include thermal polymerization initiators.

In a case in which the photocurable composition according to the present embodiment includes a thermal polymerization initiator, it is possible to carry out both the photocuring and heat curing in combination. Examples of the thermal polymerization initiator include thermal radical generators and amine compounds.

Still further, examples of the other components include: coupling agents such as silane coupling agents (for example, 3-acryloxypropyltrimethoxysilane); and additives such as rubber agents, ion-trapping agents, ion exchangers, leveling agents, plasticizers, and antifoaming agents.

The method of preparing the photocurable composition according to the present embodiment is not particularly limited. Examples thereof include a method in which the acrylic monomer (X), at least one of the (meth)acrylic monomers (A) to (C), and the photopolymerization initiator (and other component(s), if necessary) are mixed.

The means for mixing the respective components is not particularly limited. Examples thereof include: dissolution by ultrasonic wave; and mixing utilizing a twin arm mixer, a roll kneader, a twin-screw extruder, a ball mill kneader, or a planetary mixer.

The photocurable composition according to the present embodiment may be prepared by mixing the respective components, then filtering the resultant to remove impurities, and further subjecting the resultant to vacuum deaeration treatment.

A glass transition temperature (Tg) after photocuring of the photocurable composition according to the present embodiment is not particularly limited. However, the glass transition temperature (Tg) after photocuring is preferably 70° C. or higher, and more preferably 80° C. or higher, in terms of the flexural strength and the flexural modulus.

At the same time, the glass transition temperature (Tg) after photocuring is preferably 140° C. or lower, in terms of the Charpy impact strength.

[Denture Base and Plate Denture]

The dental prosthesis or the like which is a cured product (namely, stereolithographed product) of the photocurable composition according to the present embodiment is particularly preferably a denture base. The denture base which is a cured product of the photocurable composition according to the present embodiment has an excellent flexural strength, flexural modulus and Charpy impact strength.

The denture base according to the present embodiment may be a denture base for use in a complete denture or a full denture, or alternatively, a denture base for use in a partial denture.

Further, the denture base according to the present embodiment may be a denture base for an upper jaw denture (hereinafter, also referred to as "upper jaw denture base"), or a denture base for a lower jaw denture (hereinafter, also referred to as "lower jaw denture base"), or alternatively, a set of an upper jaw denture base and a lower jaw denture base.

In addition, the denture base according to the present embodiment may be a denture base in which only a portion thereof is made of the photocurable composition according to the present embodiment, or a denture base entirely made of the photocurable composition according to the present embodiment.

Examples of the denture base in which only a portion thereof is made of the photocurable composition according to the present embodiment include: a denture base (a so-called metal base) which includes a metal portion and a resin portion, and in which at least one portion of the resin portion is made of the photocurable composition according to the present embodiment; and a denture base (a so-called resin base) which consists of a resin portion, and in which only a portion of the resin portion is made of the photocurable composition according to the present embodiment.

Examples of the denture base entirely made of the photocurable composition according to the present embodiment include a denture base consisting of a resin portion.

A plate denture according to the present embodiment includes the above described denture base according to the present embodiment and an artificial tooth fixed on the denture base.

The plate denture according to the present embodiment, the denture base has an excellent flexural strength, flexural modulus and Charpy impact strength.

The plate denture according to the present embodiment may be a partial denture or a complete denture. In other words, the number of the artificial teeth to be included in the plate denture according to the present embodiment is not particularly limited, as long as the plate denture includes one artificial tooth.

Further, the plate denture according to the present embodiment may be an upper jaw denture, or a lower jaw denture, or alternatively, a set of an upper jaw denture and a lower jaw denture.

Examples of materials for the artificial tooth include an acrylic resin.

Further, the artificial tooth may contain a filler and/or the like, in addition to the acrylic resin.

EXAMPLES

The present invention is now described more specifically, with reference to Examples. However, the invention is in no way limited to these Examples.

Examples of First Embodiment

Examples (Examples 1A to 26A) and Comparative Examples (Comparative Examples 1A to 11A) of the first embodiment are described below.

Examples 1A to 26A and Comparative Examples 1A to 11A

<Preparation of Photocurable Compositions >

The components shown in the following Tables 1 to 3 were mixed to obtain photocurable compositions of Examples and Comparative Examples.

<Measurements and Evaluations>

The following measurements and evaluations were performed, using each of the resulting photocurable compositions. The results are shown in Tables 1 to 3.

(Viscosity Measurement of Photocurable Compositions)

The viscosity of each of the photocurable compositions was measured by a Type E viscometer, under conditions of 25° C. and 50 rpm.

(Flexural Strength and Flexural Modulus of Stereolithographed Products)

Each of the resulting photocurable compositions was formed into a size of 64 mm×10 mm×3.3 mm thickness using a 3D printer (MASTERr PLUS S 2011; manufactured by Carima Co., Ltd.), to obtain a formed product. The resulting formed product was subjected to irradiation of UV light having a wavelength of 365 nm, at 5 J/cm$^2$, to carry out main curing, thereby obtaining a stereolithographed product.

The resulting stereolithographed product (hereinafter, referred to as "test specimen") was stored in a constant temperature water bath maintained at 37±1° C. for 50±2 hours. Then, the test specimen was retrieved from the constant temperature water bath, and the flexural strength and the flexural modulus of the retrieved test specimen were each measured in accordance with ISO 20795-1: 2008. These measurements were carried out using a tensile test apparatus (manufactured by INTESCO Co., Ltd.), at a speed of 5±1 mm/min.

In a case in which each of the above obtained photocurable compositions is used in the production of a dental prosthesis or the like (a denture base, in particular), each stereolithographed product preferably has a flexural strength of 60 MPa or more, and more preferably 65 MPa.

Further, in this case, each photocurable composition preferably has a flexural modulus of 1,500 MPa or more, and more preferably 2,000 MPa or more.

(Charpy Impact Strength)

Each of the resulting photocurable compositions was formed into a size of 80 mm×10 mm×4 mm thickness using a 3D printer (MASTER PLUS S2011; manufactured by Carima Co., Ltd.), to obtain a formed product. The resulting formed product was subjected to irradiation of UV light having a wavelength of 365 nm, at 5 J/cm$^2$, to carry out main curing of the formed product, thereby obtaining a stereolithographed product.

The resulting stereolithographed product (hereinafter, referred to as "test specimen") was stored in a constant temperature water bath maintained at 37±1° C. for 50±2 hours.

Subsequently, the test specimen was retrieved from the constant temperature water bath, and a notch in the shape of the letter A and having a depth of 2 mm was provided at the central portion in the longitudinal direction of the retrieved test specimen, to obtain a test specimen with a single-notch. The Charpy impact strength of the resulting test specimen with a single-notch was measured in accordance with ISO 179-1: 2010 (or JIS K 7111-1: 2012). The above measurement of the Charpy impact strength was carried out under conditions of a hammer energy of 0.5 J, a swing angle of 148 degrees, a test temperature of 23° C., and edgewise impact.

In a case in which each of the above obtained photocurable compositions is used in the production of a dental prosthesis or the like (a denture base, in particular), each stereolithographed product preferably has a Charpy impact strength of 1.0 kJ/m$^2$ or more, in a view of durability.

TABLE 1

| | Components | Type | Mw | Number of ether bonds within one molecule | Example 1A | Example 2A | Example 3A | Example 4A | Example 5A | Example 6A | Example 7A | Example 8A |
|---|---|---|---|---|---|---|---|---|---|---|---|---|
| Photocurable composition | (X) | A-BPE-2 | 424 | 2 | 660 | | | | | | | |
| | | A-BPE-2.2 | 433 | 2-3 | | 660 | 700 | | | | | |
| | | ABE-300 | 469 | 3 | | | | 730 | 740 | 650 | 650 | 670 |
| | | A-BPE-4 | 513 | 4 | | | | | | | | |
| | | A-BPP-3 | 511 | 3 | | | | | | | | |
| | | BP-4PA | 569 | 4 | | | | | | | | |
| | | M-208 | 485 | 4 | | | | | | | | |
| | (A) | 2EG | 242 | 1 | | | | | 270 | | | |
| | | FA-222A | 214 | 1 | | | | | | 260 | | |
| | | 3EG-A | 258 | 2 | | | | | | | 350 | |
| | | 3PG | 328 | 2 | | | | | | | | 350 |
| | | APG-100 | 242 | 1 | 340 | 340 | | | | | | 330 |

TABLE 1-continued

|  |  | Type | Mw | Number of ether bonds within one molecule | | | | | | | | |
|---|---|---|---|---|---|---|---|---|---|---|---|---|
|  |  | APG-200 | 300 | 2 |  |  |  |  |  |  |  |  |
|  |  | SR-9003 | 328 | 2 |  | 300 |  |  |  |  |  |  |
|  | (B) | IB-XA | 208 | 0 |  |  |  |  |  |  |  |  |
|  | (C) | FA-124AS | 198 | 0 |  |  |  |  |  |  |  |  |
|  | Initiator | Ir819 |  |  | 10 | 10 | 10 | 10 | 10 | 10 | 10 | 10 |
|  |  | Ir184 |  |  |  |  |  |  |  |  |  |  |
|  |  | TPO |  |  |  |  |  |  |  |  |  |  |
| Evaluation | Viscosity (mPa·s) |  |  |  | 160 | 160 | 260 | 145 | 155 | 160 | 170 | 160 |
|  | Flexural strength (MPa) |  |  |  | 80 | 78 | 66 | 72 | 71 | 65 | 68 | 66 |
|  | Flexural modulus (MPa) |  |  |  | 2405 | 2295 | 2050 | 2020 | 2150 | 2015 | 2040 | 2020 |
|  | Charpy impact strength (kJ/m$^2$) |  |  |  | 1.3 | 1.3 | 1.2 | 1.1 | 1.2 | 1.4 | 1.1 | 1.4 |

|  | Components | Type | Mw | Number of ether bonds within one molecule | Example 9A | Example 10A | Example 11A | Example 12A | Example 13A | Example 14A | Example 15A |
|---|---|---|---|---|---|---|---|---|---|---|---|
| Photocurable composition | (X) | A-BPE-2 | 424 | 2 |  |  |  |  |  |  |  |
|  |  | A-BPE-2.2 | 433 | 2-3 |  |  |  |  |  |  |  |
|  |  | ABE-300 | 469 | 3 | 640 |  |  |  |  |  |  |
|  |  | A-BPE-4 | 513 | 4 |  | 750 | 750 |  |  |  |  |
|  |  | A-BPP-3 | 511 | 3 |  |  |  | 750 | 750 |  |  |
|  |  | BP-4PA | 569 | 4 |  |  |  |  |  | 750 | 750 |
|  |  | M-208 | 485 | 4 |  |  |  |  |  |  |  |
|  | (A) | 2EG | 242 | 1 |  | 250 |  | 250 |  | 250 |  |
|  |  | FA-222A | 214 | 1 |  |  | 250 |  | 250 |  | 250 |
|  |  | 3EG-A | 258 | 2 |  |  |  |  |  |  |  |
|  |  | 3PG | 328 | 2 |  |  |  |  |  |  |  |
|  |  | APG-100 | 242 | 1 |  |  |  |  |  |  |  |
|  |  | APG-200 | 300 | 2 | 370 |  |  |  |  |  |  |
|  |  | SR-9003 | 328 | 2 |  |  |  |  |  |  |  |
|  | (B) | IB-XA | 208 | 0 |  |  |  |  |  |  |  |
|  | (C) | FA-124AS | 198 | 0 |  |  |  |  |  |  |  |
|  | Initiator | Ir819 |  |  | 10 | 10 | 10 | 10 | 10 | 10 | 10 |
|  |  | Ir184 |  |  |  |  |  |  |  |  |  |
|  |  | TPO |  |  |  |  |  |  |  |  |  |
| Evaluation | Viscosity (mPa·s) |  |  |  | 170 | 160 | 155 | 390 | 375 | 210 | 200 |
|  | Flexural strength (MPa) |  |  |  | 67 | 66 | 65 | 68 | 67 | 67 | 66 |
|  | Flexural modulus (MPa) |  |  |  | 2030 | 2010 | 2090 | 2045 | 2120 | 2030 | 2100 |
|  | Charpy impact strength (kJ/m$^2$) |  |  |  | 1.5 | 1.1 | 1.2 | 1.1 | 1.2 | 1.2 | 1.3 |

TABLE 2

|  | Components | Type | Mw | Number of ether bonds within one molecule | Example 16A | Example 17A | Example 18A | Example 19A | Example 20A | Example 21A |
|---|---|---|---|---|---|---|---|---|---|---|
| Photocurable composition | (X) | A-BPE-2 | 424 | 2 |  |  |  |  |  |  |
|  |  | A-BPE-2.2 | 433 | 2-3 |  |  | 660 |  |  |  |
|  |  | ABE-300 | 469 | 3 |  |  |  | 740 |  | 730 |
|  |  | A-BPE-4 | 513 | 4 |  |  |  |  | 750 |  |
|  |  | A-BPP-3 | 511 | 3 |  |  |  |  |  |  |
|  |  | BP-4PA | 569 | 4 |  |  |  |  |  |  |
|  |  | M-208 | 485 | 4 | 750 | 750 |  |  |  |  |
|  | (A) | 2EG | 242 | 1 | 250 |  |  |  | 250 | 140 |
|  |  | FA-222A | 214 | 1 |  | 250 |  | 260 |  |  |
|  |  | 3EG-A | 258 | 2 |  |  |  |  |  |  |
|  |  | 3PG | 328 | 2 |  |  |  |  |  |  |
|  |  | APG-100 | 242 | 1 |  |  | 340 |  |  |  |
|  |  | APG-200 | 300 | 2 |  |  |  |  |  |  |
|  |  | SR-9003 | 328 | 2 |  |  |  |  |  |  |
|  | (B) | IB-XA | 208 | 0 |  |  |  |  |  | 130 |
|  | (C) | FA-124AS | 198 | 0 |  |  |  |  |  |  |
|  | Initiator | Ir819 |  |  | 10 | 10 |  |  |  | 10 |
|  |  | Ir184 |  |  |  |  | 10 | 10 | 10 |  |
|  |  | TPO |  |  |  |  | 10 | 10 | 10 |  |
| Evaluation | Viscosity (mPa·s) |  |  |  | 100 | 95 | 170 | 160 | 170 | 175 |
|  | Flexural strength (MPa) |  |  |  | 67 | 66 | 77 | 70 | 67 | 75 |
|  | Flexural modulus (MPa) |  |  |  | 2010 | 2070 | 2280 | 2130 | 2020 | 2090 |
|  | Charpy impact strength (kJ/m$^2$) |  |  |  | 1.4 | 1.6 | 1.3 | 1.2 | 1.1 | 1.1 |

TABLE 2-continued

| | Components | Type | Mw | Number of ether bonds within one molecule | Example 22A | Example 23A | Example 24A | Example 25A | Example 26A |
|---|---|---|---|---|---|---|---|---|---|
| Photocurable composition | (X) | A-BPE-2 | 424 | 2 | | | | | |
| | | A-BPE-2.2 | 433 | 2-3 | | | | | |
| | | ABE-300 | 469 | 3 | 730 | 730 | 740 | 740 | 740 |
| | | A-BPE-4 | 513 | 4 | | | | | |
| | | A-BPP-3 | 511 | 3 | | | | | |
| | | BP-4PA | 569 | 4 | | | | | |
| | | M-208 | 485 | 4 | | | | | |
| | (A) | 2EG | 242 | 1 | 140 | 140 | | | |
| | | FA-222A | 214 | 1 | | | 135 | 135 | 135 |
| | | 3EG-A | 258 | 2 | | | | | |
| | | 3PG | 328 | 2 | | | | | |
| | | APG-100 | 242 | 1 | | | | | |
| | | APG-200 | 300 | 2 | | | | | |
| | | SR-9003 | 328 | 2 | | | | | |
| | (B) | IB-XA | 208 | 0 | 65 | | 125 | 65 | |
| | (C) | FA-124AS | 198 | 0 | 65 | 130 | | 60 | 125 |
| | Initiator | Ir819 | | | 10 | 10 | 10 | 10 | 10 |
| | | Ir184 | | | | | | | |
| | | TPO | | | | | | | |
| Evaluation | Viscosity (mPa·s) | | | | 140 | 120 | 185 | 150 | 130 |
| | Flexural strength (MPa) | | | | 73 | 68 | 75 | 70 | 67 |
| | Flexural modulus (MPa) | | | | 2060 | 2030 | 2150 | 2110 | 2070 |
| | Charpy impact strength (kJ/m$^2$) | | | | 1.1 | 1.1 | 1.1 | 1.1 | 1.1 |

TABLE 3

| | Components | Type | Mw | Number of ether bonds within one molecule | Comparative Example 1A | Comparative Example 2A | Comparative Example 3A | Comparative Example 4A | Comparative Example 5A | Comparative Example 6A |
|---|---|---|---|---|---|---|---|---|---|---|
| Photocurable composition | (X) | A-BPE-2 | 424 | 2 | | | | | | |
| | | A-BPE-2.2 | 433 | 2-3 | | | | | | |
| | | ABE-300 | 469 | 3 | | | | | | 600 |
| | | A-BPE-4 | 513 | 4 | | | | | | |
| | | A-BPP-3 | 511 | 3 | | | | | | |
| | | BP-4PA | 569 | 4 | | | | | | |
| | | M-208 | 485 | 4 | | | | | | |
| | (A) | 2EG | 242 | 1 | 250 | 250 | 220 | | | |
| | | FA-222A | 214 | 1 | | | | | | |
| | | 3EG-A | 258 | 2 | | | | | | |
| | | 3PG | 328 | 2 | | | | 300 | | |
| | | APG-100 | 242 | 1 | | | | | 280 | |
| | | APG-200 | 300 | 2 | | | | | | |
| | | SR-9003 | 328 | 2 | | | | | | |
| | (B) | IB-XA | 208 | 0 | | | | | | |
| | (C) | FA-124AS | 198 | 0 | | | | | | |
| | Other monomer | A-BPE-10 | 777 | 10 | 750 | | | | | |
| | | A-BPE-20 | 1217 | 20 | | 750 | | | | |
| | | BP-2EM | 479 | 2-3 | | | 780 | 700 | 720 | |
| | | FA-240A | 523 | 8 | | | | | | 400 |
| | | APG-400 | 533 | 6 | | | | | | |
| | | CD9043 | 677 | | | | | | | |
| | | FA-PTG9A | 775 | 8 | | | | | | |
| | | DMGDA | 186 | 1 | | | | | | |
| | | 9PG | 561 | 6 | | | | | | |
| | Initiator | Ir819 | | | 10 | 10 | 10 | 10 | 10 | 10 |
| | | Ir184 | | | | | | | | |
| | | TPO | | | | | | | | |
| Evaluation | Viscosity (mPa·s) | | | | 170 | 160 | 160 | 160 | 140 | 250 |
| | Flexural strength (MPa) | | | | 35 | 15 | 94 | 72 | 75 | 25 |
| | Flexural modulus (MPa) | | | | 850 | 220 | 2615 | 2340 | 2205 | 670 |
| | Charpy impact strength (kJ/m$^2$) | | | | 1.8 | 1.5 | 0.6 | 0.6 | 0.6 | 1.8 |

TABLE 3-continued

| Components | | Type | Mw | Number of ether bonds within one molecule | Comparative Example 7A | Comparative Example 8A | Comparative Example 9A | Comparative Example 10A | Comparative Example 11A |
|---|---|---|---|---|---|---|---|---|---|
| Photocurable composition | (X) | A-BPE-2 | 424 | 2 | | | | | |
| | | A-BPE-2.2 | 433 | 2-3 | | | | | |
| | | ABE-300 | 469 | 3 | 600 | 600 | 600 | 600 | 600 |
| | | A-BPE-4 | 513 | 4 | | | | | |
| | | A-BPP-3 | 511 | 3 | | | | | |
| | | BP-4PA | 569 | 4 | | | | | |
| | | M-208 | 485 | 4 | | | | | |
| | (A) | 2EG | 242 | 1 | | | | | |
| | | FA-222A | 214 | 1 | | | | | |
| | | 3EG-A | 258 | 2 | | | | | |
| | | 3PG | 328 | 2 | | | | | |
| | | APG-100 | 242 | 1 | | | | | |
| | | APG-200 | 300 | 2 | | | | | |
| | | SR-9003 | 328 | 2 | | | | | |
| | (B) | IB-XA | 208 | 0 | | | | | |
| | (C) | FA-124AS | 198 | 0 | | | | | |
| | Other monomer | A-BPE-10 | 777 | 10 | | | | | |
| | | A-BPE-20 | 1217 | 20 | | | | | |
| | | BP-2EM | 479 | 2-3 | | | | | |
| | | FA-240A | 523 | 8 | | | | | |
| | | APG-400 | 533 | 6 | 400 | | | | |
| | | CD9043 | 677 | | | 400 | | | |
| | | FA-PTG9A | 775 | 8 | | | 400 | | |
| | | DMGDA | 186 | 1 | | | | 400 | |
| | | 9PG | 561 | 6 | | | | | 400 |
| | Initiator | Ir819 | | | 10 | 10 | 10 | 10 | 10 |
| | | Ir184 | | | | | | | |
| | | TPO | | | | | | | |
| Evaluation | | Viscosity (mPa·s) | | | 190 | 260 | 430 | 100 | 170 |
| | | Flexural strength (MPa) | | | 30 | 18 | 10 | 95 | 45 |
| | | Flexural modulus (MPa) | | | 720 | 280 | 120 | 2925 | 1020 |
| | | Charpy impact strength (kJ/m$^2$) | | | 1.9 | 1.3 | 1.4 | 0.6 | 1.5 |

—Description of Tables 1 to 3—

In Tables 1 to 3,
each of the amounts (numbers) of the components in each of the Examples and Comparative Examples is shown in "parts by mass";
"(X)" denotes acrylic monomer (X);
"(A)" denotes (meth)acrylic monomer (A);
"(B)" denotes (meth)acrylic monomer (B);
"(C)" denotes (meth)acrylic monomer (C);
the term "Other monomer" denotes a (meth)acrylic monomers other than the (meth)acrylic monomers (A) to (C); and the term "Initiator" denotes a photopolymerization initiator.

The same applies for Tables 4 to 9 to be described later.

The respective structures of the acrylic monomers (X) listed in Tables 1 to 3 are as shown below.

In Tables 1 to 3, A-BPE-2, A-BPE-2.2, ABE-300, A-BPE-4, and A-BPP-3 are acrylic monomers manufactured by Shin Nakamura Chemical Co., Ltd.; BP-4PA is an acrylic monomer manufactured by Kyoeisha Chemical Co. Ltd.; and M-208 is an acrylic monomer manufactured by TOAGOSEI CO., LTD. The same applies for Tables 4 to 9 to be described later.

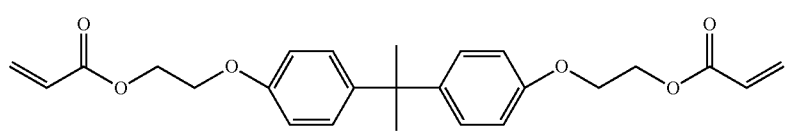

A-BPE-2

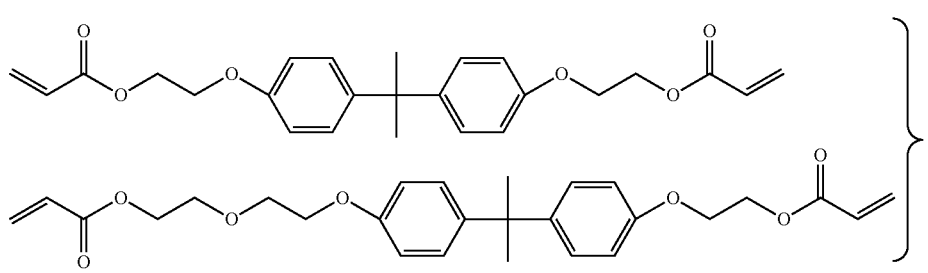

A-BPE-2.2

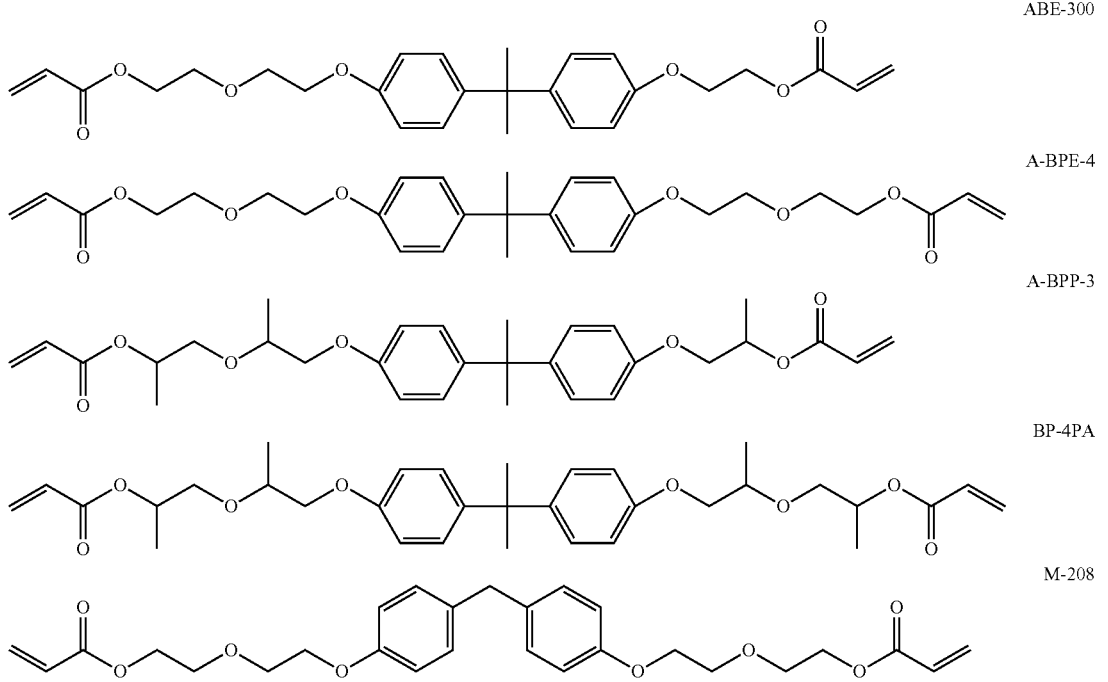

The respective structures of (meth)acrylic monomers (A) listed in Tables 1 to 3 are as shown below.

In Tables 1 to 3, 2EG is a methacrylic monomer manufactured by Kyoeisha Chemical Co. Ltd.; 3PG is a methacrylic monomer manufactured by Shin Nakamura Chemical Co., Ltd.; FA-222A is an acrylic monomer manufactured by Hitachi Chemical Co., Ltd.; 3EG-A is an acrylic monomer manufactured by Kyoeisha Chemical Co. Ltd.; APG-100 and APG-200 are acrylic monomers manufactured by Shin Nakamura Chemical Co., Ltd.; and SR 9003 is an acrylic monomer manufactured by Arkema Inc.

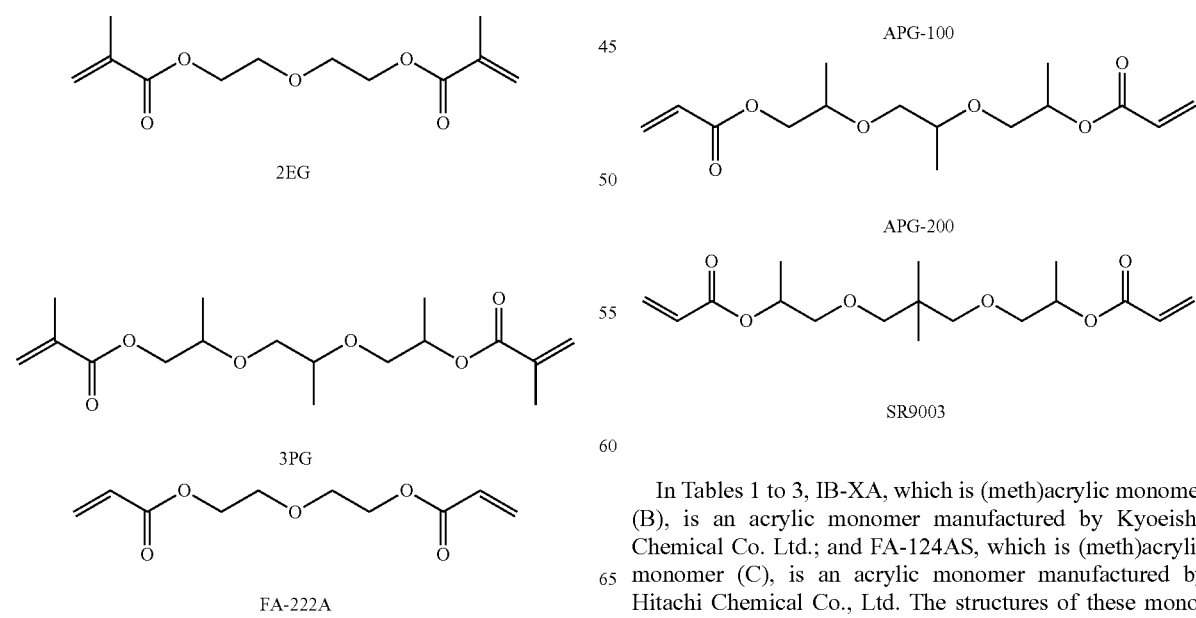

In Tables 1 to 3, IB-XA, which is (meth)acrylic monomer (B), is an acrylic monomer manufactured by Kyoeisha Chemical Co. Ltd.; and FA-124AS, which is (meth)acrylic monomer (C), is an acrylic monomer manufactured by Hitachi Chemical Co., Ltd. The structures of these monomers are as shown below.

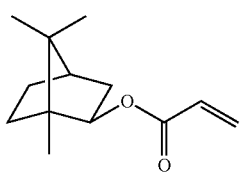

IB-XA

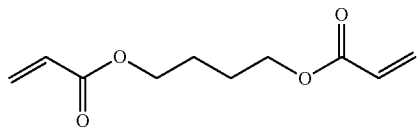

FA-124AS

The structures of the other monomers listed in Table 3 are as shown below.

In Table 3, A-BPE-10, A-BPE-20, APG-400, and 9PG are acrylic monomers manufactured by Shin Nakamura Chemical Co., Ltd.; FA-240A and FA-PTG9A are acrylic monomers manufactured by Hitachi Chemical Co., Ltd.; CD 9043 is an acrylic monomer manufactured by Arkema Inc.; and BP-2EM is a methacrylic monomer manufactured by Kyoeisha Chemical Co. Ltd.

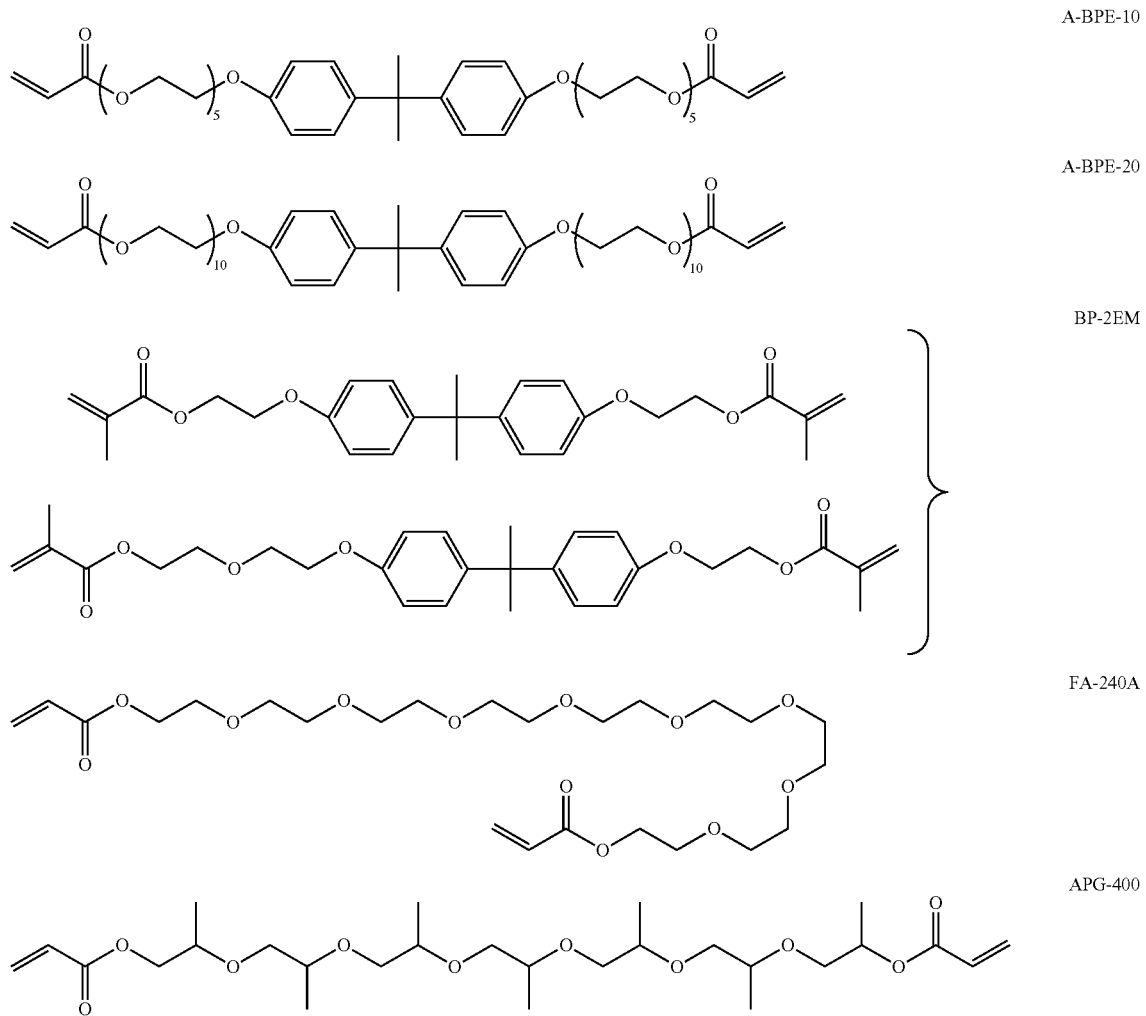

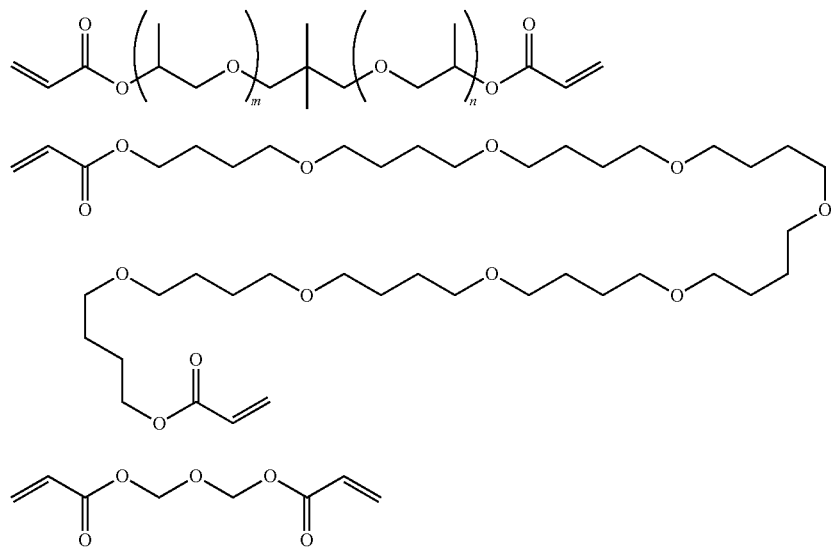

CD9043

FA-PTG9A

DMGDA

9PG

In Tables 1 to 3, the term "Initiator" denotes photopolymerization initiators.

Of the initiators (namely, the photopolymerization initiators) listed in Tables 1 to 3, Irg 819 is "Irgacure 819" (an acylphosphine oxide compound) manufactured by BASF Japan Ltd.; Irg 184 is "Irgacure 184" (an alkylphenone compound) manufactured by BASF Japan Ltd.; and TPO is "Irgacure TPO" (an acylphosphine oxide compound) manufactured by BASF Japan Ltd. The respective structures of these photopolymerization initiators are as shown below.

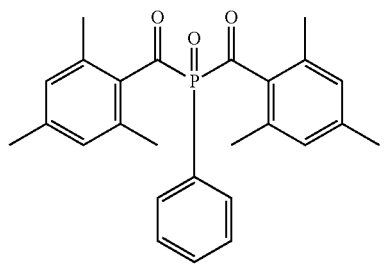

Irg819

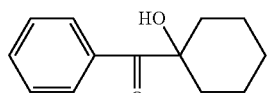

Irg184

-continued

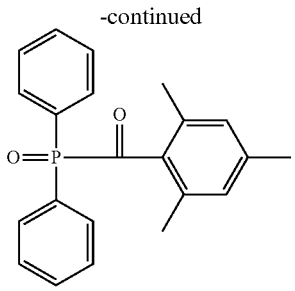

TPO

As shown in Tables 1 to 3, in each of Examples 1A to 26A, a photocurable composition was used which includes: the acrylic monomer (X) which is a diacrylic monomer containing two aromatic rings and two acryloyloxy groups within one molecule, and having a weight average molecular weight of from 400 to 580; the (meth)acrylic monomer (A) which is a di(meth)acrylic monomer not containing, within one molecule, an aromatic ring and containing, within one molecule, one or more ether bonds and two (meth)acryloyloxy groups, and having a weight average molecular weight of from 200 to 400; and the photopolymerization initiator(s). As a result, it was possible to obtain a stereolithographed product which satisfies all of: a flexural strength of 60 MPa or more, a flexural modulus of 1,500 MPa or more, and a Charpy impact strength of 1.0 kJ/m² or more, in each of Examples 1A to 26A. Further, the photocurable compositions of Examples 1A to 26A had a viscosity suitable for stereolithography.

The above results confirmed that each of the photocurable compositions of Examples 1A to 26A is suitable for the production by stereolithography of a dental prosthesis or the like (a denture base, in particular).

In contrast to Examples 1A to 26A, in Comparative Examples 1A and 2A, in each of which a diacrylic monomer (A-BPE-10 or A-BPE-20) containing two aromatic rings and two acryloyloxy groups within one molecule and having a weight average molecular weight of greater than 580 was used instead of the acrylic monomer (X), the resulting stereolithographed products had an insufficient flexural strength and flexural modulus.

In Comparative Examples 3A to 5A, in each of which BP-2EM, which is a methacrylic monomer, not an acrylic monomer, containing two aromatic rings and two acryloyloxy groups within one molecule and having a weight average molecular weight of from 400 to 580 was used instead of the acrylic monomer (X), the resulting stereolithographed products had an insufficient Charpy impact strength.

In Comparative Examples 6A to 9A and 11A, in each of which a di(meth)acrylic monomer (FA-240A, APG-400, CD 9043, FA-PTG9A, or 9PG) not containing, within one molecule, an aromatic ring and containing, within one molecule, one or more ether bonds and two (meth)acryloyloxy groups, and having a weight average molecular weight of greater than 400, was used instead of the (meth)acrylic monomer (A), the resulting stereolithographed products had an insufficient flexural strength and flexural modulus.

Further, in Comparative Example 10A in which a di(meth)acrylic monomer (DMGDA) not containing, within one molecule, an aromatic ring and containing, within one molecule, one or more ether bonds and two (meth)acryloyloxy groups, and having a weight average molecular weight of less than 200, was used instead of the (meth)acrylic monomer (A), the resulting stereolithographed product had an insufficient Charpy impact strength.

Examples of Second Embodiment

Examples (Examples 1B to 26B) and Comparative Examples (Comparative Examples 1B to 12B) of the second embodiment are described below.

Examples 1B to 26B and Comparative Examples 1B to 12B

<Preparation of Photocurable Compositions>

The components shown in the following Tables 4 to 6 were mixed to obtain photocurable compositions of Examples and Comparative Examples.

<Measurements and Evaluations>

Using each of the resulting photocurable compositions, the following measurements and evaluations were performed, in the same manner as described in Example 1A. The results are shown in Tables 4 to 6.

TABLE 4

| Components | | Type | Mw | Number of ether bonds within one molecule | Example 1B | Example 2B | Example 3B | Example 4B | Example 5B | Example 6B | Example 7B | Example 8B |
|---|---|---|---|---|---|---|---|---|---|---|---|---|
| Photocurable composition | (X) | A-BPE-2 | 424 | 2 | 600 | | | | | | | |
| | | A-BPE-2.2 | 433 | 2-3 | | 600 | | | | | | |
| | | ABE-300 | 469 | 3 | | | 660 | 660 | 660 | 780 | 780 | 720 |
| | | A-BPE-4 | 513 | 4 | | | | | | | | |
| | | A-BPP-3 | 511 | 3 | | | | | | | | |
| | | BP-4PA | 569 | 4 | | | | | | | | |
| | | M-208 | 485 | 4 | | | | | | | | |
| | (B) | IB-XA | 208 | 0 | 400 | 400 | 340 | | | | | |
| | | FA-513AS | 206 | 0 | | | | 340 | | | | |
| | | FA-511AS | 204 | 0 | | | | | 340 | | | |
| | | CHA | 154 | 0 | | | | | | 220 | | |
| | | THFA | 156 | 0 | | | | | | | 220 | |
| | | SR217 | 210 | 0 | | | | | | | | 280 |
| | | ACMO | 141 | 0 | | | | | | | | |
| | (A) | FA-222A | 214 | 1 | | | | | | | | |
| | (C) | FA124AS | 198 | 0 | | | | | | | | |
| | Initiator | Ir819 | | | 10 | 10 | 10 | 10 | 10 | 10 | 10 | 10 |
| | | Irl84 | | | | | | | | | | |
| | | TPO | | | | | | | | | | |
| Evaluation | | Viscosity (mPa·s) | | | 190 | 170 | 140 | 170 | 170 | 160 | 160 | 160 |
| | | Flexural strength (MPa) | | | 85 | 82 | 79 | 85 | 71 | 73 | 66 | 65 |
| | | Flexural modulus (MPa) | | | 2550 | 2300 | 2170 | 2250 | 2070 | 2080 | 2080 | 2020 |
| | | Charpy impact strength (kJ/m$^2$) | | | 1.0 | 1.0 | 1.0 | 1.1 | 1.1 | 1.3 | 1.5 | 1.3 |

| Components | | Type | Mw | Number of ether bonds within one molecule | Example 9B | Example 10B | Example 11B | Example 12B | Example 133B | Example 14B | Example 15B |
|---|---|---|---|---|---|---|---|---|---|---|---|
| Photocurable composition | (X) | A-BPE-2 | 424 | 2 | | | | | | | |
| | | A-BPE-2.2 | 433 | 2-3 | | | | | | | |
| | | ABE-300 | 469 | 3 | 630 | | | | | | |
| | | A-BPE-4 | 513 | 4 | | 750 | 750 | | | | |
| | | A-BPP-3 | 511 | 3 | | | | 750 | 750 | | |
| | | BP-4PA | 569 | 4 | | | | | | 750 | 750 |
| | | M-208 | 485 | 4 | | | | | | | |

TABLE 4-continued

| Components | | Type | Mw | Number of ether bonds within one molecule | | | | | | | |
|---|---|---|---|---|---|---|---|---|---|---|---|
| | (B) | IB-XA | 208 | 0 | | 250 | | 250 | | 250 | |
| | | FA-513AS | 206 | 0 | | | 250 | | 250 | | 250 | 250 |
| | | FA-511AS | 204 | 0 | | | | | | | | |
| | | CHA | 154 | 0 | | | | | | | | |
| | | THFA | 156 | 0 | | | | | | | | |
| | | SR217 | 210 | 0 | | | | | | | | |
| | | ACMO | 141 | 0 | 370 | | | | | | | |
| | (A) | FA-222A | 214 | 1 | | | | | | | | |
| | (C) | FA124AS | 198 | 0 | | | | | | | | |
| | Initiator | Ir819 | | | 10 | 10 | 10 | 10 | 10 | 10 | 10 |
| | | Ir184 | | | | | | | | | |
| | | TPO | | | | | | | | | |
| Evaluation | | Viscosity (mPa·s) | | | 150 | 260 | 280 | 255 | 270 | 220 | 230 |
| | | Flexural strength (MPa) | | | 68 | 70 | 73 | 69 | 71 | 66 | 67 |
| | | Flexural modulus (MPa) | | | 2030 | 2035 | 2050 | 2060 | 2080 | 2020 | 2040 |
| | | Charpy impact strength (kJ/m²) | | | 1.3 | 1.0 | 1.1 | 1.2 | 1.3 | 1.3 | 1.4 |

TABLE 5

| | Components | Type | Mw | Number of ether bonds within one molecule | Example 16B | Example 17B | Example 18B | Example 19B | Example 20B | Example 21B |
|---|---|---|---|---|---|---|---|---|---|---|
| Photocurable composition | (X) | A-BPE-2 | 424 | 2 | | | | | | |
| | | A-SPE-2.2 | 433 | 2-3 | | | 600 | | | |
| | | ABE-300 | 469 | 3 | | | | 660 | | 660 |
| | | A-BPE-4 | 513 | 4 | | | | | 750 | |
| | | A-BPP-3 | 511 | 3 | | | | | | |
| | | BP-4PA | 569 | 4 | | | | | | |
| | | M-208 | 485 | 4 | 750 | 750 | | | | |
| | (B) | IB-XA | 208 | 0 | 250 | | 400 | 340 | 250 | 175 |
| | | FA-513AS | 206 | 0 | | 250 | | | | |
| | | FA-511AS | 204 | 0 | | | | | | |
| | | CHA | 154 | 0 | | | | | | |
| | | THFA | 156 | 0 | | | | | | |
| | | SR217 | 210 | 0 | | | | | | |
| | | ACMO | 141 | 0 | | | | | | |
| | (A) | FA-222A | 214 | 1 | | | | | | 165 |
| | (C) | FA124AS | 198 | 0 | | | | | | |
| | Initiator | Ir819 | | | 10 | 10 | | | | 10 |
| | | Ir184 | | | | | 10 | 10 | 10 | |
| | | TPO | | | | | 10 | 10 | 10 | |
| Evaluation | | Viscosity (mPa·s) | | | 110 | 105 | 180 | 150 | 270 | 120 |
| | | Flexural strength (MPa) | | | 65 | 66 | 81 | 78 | 71 | 74 |
| | | Flexural modulus (MPa) | | | 2010 | 2035 | 2280 | 2190 | 2050 | 2140 |
| | | Charpy impact strength (kJ/m²) | | | 1.5 | 1.6 | 1.1 | 1.1 | 1.1 | 1.1 |

| | Components | Type | Mw | Number of ether bonds within one molecule | Example 22B | Example 23B | Example 24B | Example 25B | Example 26B |
|---|---|---|---|---|---|---|---|---|---|
| Photocurable composition | (X) | A-BPE-2 | 424 | 2 | | | | | |
| | | A-SPE-2.2 | 433 | 2-3 | | | | | |
| | | ABE-300 | 469 | 3 | 660 | 660 | 660 | 660 | 660 |
| | | A-BPE-4 | 513 | 4 | | | | | |
| | | A-BPP-3 | 511 | 3 | | | | | |
| | | BP-4PA | 569 | 4 | | | | | |
| | | M-208 | 485 | 4 | | | | | |
| | (B) | IB-XA | 208 | 0 | 175 | 175 | | | |
| | | FA-513AS | 206 | 0 | | | 175 | 175 | 175 |
| | | FA-511AS | 204 | 0 | | | | | |
| | | CHA | 154 | 0 | | | | | |
| | | THFA | 156 | 0 | | | | | |
| | | SR217 | 210 | 0 | | | | | |
| | | ACMO | 141 | 0 | | | | | |
| | (A) | FA-222A | 214 | 1 | 85 | | 165 | 85 | |
| | (C) | FA124AS | 198 | 0 | 80 | 165 | | 80 | 165 |
| | Initiator | Ir819 | | | 10 | 10 | 10 | 10 | |
| | | Ir184 | | | | | | | |
| | | TPO | | | | | | | |

TABLE 5-continued

| | | | | | | |
|---|---|---|---|---|---|---|
| Evaluation | Viscosity (mPa·s) | 115 | 110 | 140 | 130 | 125 |
| | Flexural strength (MPa) | 72 | 71 | 78 | 74 | 73 |
| | Flexural modulus (MPa) | 2120 | 2110 | 2190 | 2130 | 2090 |
| | Charpy impact strength (kJ/m$^2$) | 1.1 | 1.0 | 1.1 | 1.1 | 1.1 |

TABLE 6

| Components | | Type | Mw | Number of ether bonds within one molecule | Comparative Example 1B | Comparative Example 2B | Comparative Example 3B | Comparative Example 4B | Comparative Example 5B | Comparative Example 6B | Comparative Example 7B |
|---|---|---|---|---|---|---|---|---|---|---|---|
| Photo-curable composition | (X) | A-BPE-2 | 424 | 2 | | | | | | | |
| | | A-BPE-2.2 | 433 | 2-3 | | | | | | | |
| | | ABE-300 | 469 | 3 | | | | | | 700 | 600 |
| | | A-BPE-4 | 513 | 4 | | | | | | | |
| | | A-BPP-3 | 511 | 3 | | | | | | | |
| | | BP-4PA | 569 | 4 | | | | | | | |
| | | M-208 | 485 | 4 | | | | | | | |
| | (B) | IB-XA | 208 | 0 | 250 | 250 | 200 | | | | |
| | | FA-513AS | 206 | 0 | | | | 200 | | | |
| | | FA-511AS | 204 | 0 | | | | | | | |
| | | CHA | 154 | 0 | | | | | 200 | | |
| | | THFA | 156 | 0 | | | | | | | |
| | | SR217 | 210 | 0 | | | | | | | |
| | | ACMO | 141 | 0 | | | | | | | |
| | (A) | FA-222A | 214 | 1 | | | | | | | |
| | (C) | FA124AS | 198 | 0 | | | | | | | |
| | Other monomers | A-BPE-10 | 777 | 10 | 750 | | | | | | |
| | | A-BPE-20 | 1217 | 20 | | 750 | | | | | |
| | | BP-2EM | 479 | 2-3 | | | 800 | 800 | 800 | | |
| | | SR611 | 272 | 2 | | | | | | 300 | |
| | | M-140 | 251 | 0 | | | | | | | 400 |
| | | AIB | 128 | 0 | | | | | | | |
| | | NOAA | 184 | 0 | | | | | | | |
| | | LA | 240 | 0 | | | | | | | |
| | | CPA | 112 | 0 | | | | | | | |
| | | CBA | 126 | 0 | | | | | | | |
| | Initiators | Ir819 | | | 10 | 10 | 10 | 10 | 10 | 10 | 10 |
| | | Ir184 | | | | | | | | | |
| | | TPO | | | | | | | | | |
| Evaluation | Viscosity (mPa·s) | | | | 160 | 150 | 170 | 180 | 110 | 90 | 900 |
| | Flexural strength (MPa) | | | | 45 | 30 | 88 | 84 | 78 | 40 | 50 |
| | Flexural modulus (MPa) | | | | 1150 | 780 | 2650 | 2540 | 2305 | 1350 | 1400 |
| | Charpy impact strength (kJ/m$^2$) | | | | 2.0 | 2.1 | 0.6 | 0.6 | 0.6 | 1.7 | 2.2 |

| Components | | Type | Mw | Number of ether bonds within one molecule | Comparative Example 8B | Comparative Example 9B | Comparative Example 10B | Comparative Example 11B | Comparative Example 12B |
|---|---|---|---|---|---|---|---|---|---|
| Photo-curable composition | (X) | A-BPE-2 | 424 | 2 | | | | | |
| | | A-BPE-2.2 | 433 | 2-3 | | | | | |
| | | ABE-300 | 469 | 3 | 800 | 800 | 800 | 800 | 800 |
| | | A-BPE-4 | 513 | 4 | | | | | |
| | | A-BPP-3 | 511 | 3 | | | | | |
| | | BP-4PA | 569 | 4 | | | | | |
| | | M-208 | 485 | 4 | | | | | |
| | (B) | IB-XA | 208 | 0 | | | | | |
| | | FA-513AS | 206 | 0 | | | | | |
| | | FA-511AS | 204 | 0 | | | | | |
| | | CHA | 154 | 0 | | | | | |
| | | THFA | 156 | 0 | | | | | |
| | | SR217 | 210 | 0 | | | | | |
| | | ACMO | 141 | 0 | | | | | |
| | (A) | FA-222A | 214 | 1 | | | | | |
| | (C) | FA124AS | 198 | 0 | | | | | |
| | Other monomers | A-BPE-10 | 777 | 10 | | | | | |
| | | A-BPE-20 | 1217 | 20 | | | | | |
| | | BP-2EM | 479 | 2-3 | | | | | |
| | | SR611 | 272 | 2 | | | | | |
| | | M-140 | 251 | 0 | | | | | |

TABLE 6-continued

| | | | | | | | | | |
|---|---|---|---|---|---|---|---|---|---|
| | | AIB | 128 | 0 | 200 | | | | |
| | | NOAA | 184 | 0 | | 200 | | | |
| | | LA | 240 | 0 | | | 200 | | |
| | | CPA | 112 | 0 | | | | 200 | |
| | | CBA | 126 | 0 | | | | | 200 |
| | Initiators | Ir819 | | | | | | | |
| | | Ir184 | | | | | | | |
| | | TPO | | | | | | | |
| Evaluation | Viscosity (mPa·s) | | | | 70 | 85 | 100 | 150 | 170 |
| | Flexural strength (MPa) | | | | 15 | 20 | 35 | 75 | 74 |
| | Flexural modulus (MPa) | | | | 190 | 250 | 780 | 2215 | 2165 |
| | Charpy impact strength (kJ/m$^2$) | | | | 1.9 | 2.1 | 2.2 | 0.7 | 0.9 |

—Description of Tables 4 to 6—

In Tables 4 to 6, each of the acrylic monomers (X) is the same as that described in the "Description of Tables 1 to 3" above.

Of the (meth)acrylic monomers (B) listed in Tables 4 to 6, FA-513 AS and FA-511 AS are acrylic monomers manufactured by Hitachi Chemical Co., Ltd.; CHA and THFA are acrylic monomers manufactured by Osaka Organic Chemical Industry Ltd.; SR217 is an acrylic monomer manufactured by Arkema Inc.; and ACMO is an acrylic monomer manufactured by KJ Chemicals Corporation. The structures of these monomers are as shown below.

Of the (meth)acrylic monomers (B) listed in Tables 4 to 6, IB-XA is the same as that described in the "Description of Tables 1 to 3" above.

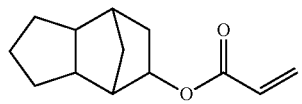

FA-513AS

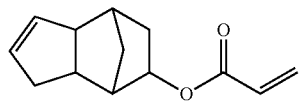

FA-511AS

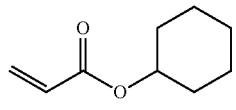

CHA

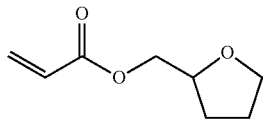

THFA

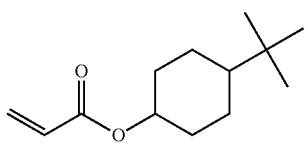

SR217

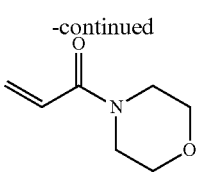

ACMO

In Tables 4 to 6, each of FA-222A, which is the (meth)acrylic monomer (A), and FA-124 AS, which is the (meth)acrylic monomer (C), is the same as that described in the "Description of Tables 1 to 3" above.

Of the other (meth)acrylic monomers listed in Tables 4 to 6, each of A-BPE-10, A-BPE-20, and BP-2EM is the same as that described in the "Description of Tables 1 to 3" above.

The rest of the other (meth)acrylic monomers listed in Tables 4 to 6, other than those described above, have the structures as shown below.

SR611 is an acrylic monomer manufactured by Arkema Inc.; M-140 is an acrylic monomer manufactured by Toagosei Co., Ltd.; and AIB, NOAA and LA are acrylic monomers manufactured by Osaka Organic Chemical Industry Ltd.

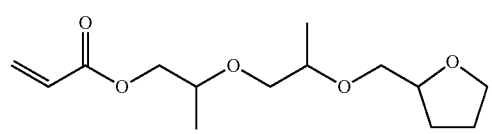

SR611

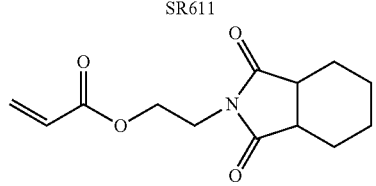

M-140

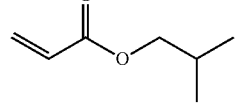

AIB

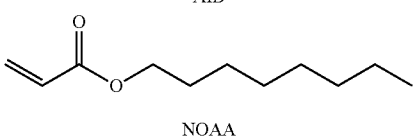

NOAA

-continued

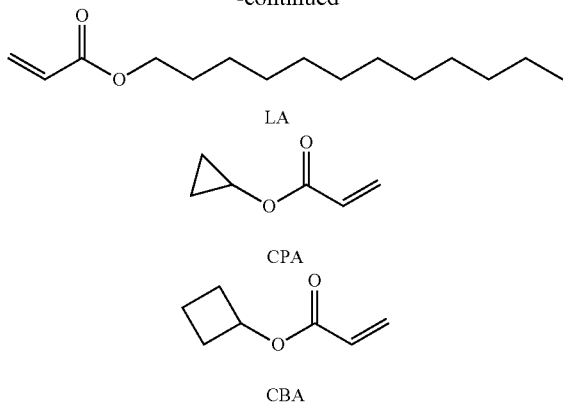

LA

CPA

CBA

In Tables 4 to 6, the term "Initiator" denotes photopolymerization initiators.

Each of the initiators (namely, the photopolymerization initiators) listed in Tables 4 to 6 is the same as that described in the "Description of Tables 1 to 3" above.

As shown in Tables 4 to 6, in each of Examples 1B to 26B, a photocurable composition was used which includes: the acrylic monomer (X) which is a diacrylic monomer containing two aromatic rings and two acryloyloxy groups within one molecule, and having a weight average molecular weight of from 400 to 580; the (meth)acrylic monomer (B) which is a (meth)acrylic monomer containing a ring structure other than an aromatic ring and one (meth)acryloyloxy group within one molecule, and having a weight average molecular weight of from 130 to 240; and the photopolymerization initiator(s). As a result, it was possible to obtain a stereolithographed product which satisfies all of: a flexural strength of 60 MPa or more, a flexural modulus of 1,500 MPa or more, and a Charpy impact strength of 1.0 kJ/m$^2$ or more, in each of Examples 1B to 26B. Further, the photocurable compositions of Examples 1B to 26B had a viscosity suitable for stereolithography.

The above results confirmed that each of the photocurable compositions of Examples 1B to 26B is suitable for the production by stereolithography of a dental prosthesis or the like (a denture base, in particular).

In contrast to Examples 1B to 26B, in Comparative Examples 1B and 2B, in each of which a diacrylic monomer (A-BPE-10 or A-BPE-20) containing two aromatic rings and two acryloyloxy groups within one molecule and having a weight average molecular weight of greater than 580 was used instead of the acrylic monomer (X), the resulting stereolithographed products had an insufficient flexural strength and flexural modulus.

In Comparative Examples 3B to 5B, in each of which BP-2EM, which is a methacrylic monomer, not an acrylic monomer, containing two aromatic rings and two acryloyloxy groups within one molecule and having a weight average molecular weight of from 400 to 580, was used instead of the acrylic monomer (X), the resulting stereolithographed products had an insufficient Charpy impact strength.

In Comparative Examples 6B and 7B, in each of which a (meth)acrylic monomer (SR611 or M-140) containing a ring structure other than an aromatic ring and one (meth)acryloyloxy group within one molecule, and having a weight average molecular weight of greater than 240, was used instead of the (meth)acrylic monomer (B), the resulting stereolithographed products had an insufficient flexural strength and flexural modulus.

In Comparative Examples 8B to 10B, in each of which a (meth)acrylic monomer (AIB, NOAA or LA) not containing a ring structure within one molecule was used instead of the (meth)acrylic monomer (B), the resulting stereolithographed products also had an insufficient flexural strength and flexural modulus.

Further, in Comparative Examples 11B and 12B, in each of which a (meth)acrylic monomer (CPA or CBA) containing a ring structure other than an aromatic ring and one (meth)acryloyloxy group within one molecule, and having a weight average molecular weight of less than 130, was used instead of the (meth)acrylic monomer (B), the resulting stereolithographed products had an insufficient Charpy impact strength.

Examples of Third Embodiment

Examples (Examples 1C to 26C) and Comparative Examples (Comparative Examples 1C to 9C) of the third embodiment are described below.

Examples 1C to 26C and Comparative Examples 1C to 9C

<Preparation of Photocurable Compositions>

The components shown in the following Tables 7 to 9 were mixed to obtain photocurable compositions of Examples and Comparative Examples.

<Measurements and Evaluations>

Using each of the resulting photocurable compositions, the following measurements and evaluations were performed, in the same manner as described in Example 1A. The results are shown in Tables 7 to 9.

TABLE 7

| | Components | Type | Mw | Number of ether bonds within one molecule | Example 1C | Example 2C | Example 3C | Example 4C | Example 5C | Example 6C | Example 7C | Example 8C |
|---|---|---|---|---|---|---|---|---|---|---|---|---|
| Photocurable composition | (X) | A-BPE-2 | 424 | 2 | 700 | | | | | | | |
| | | A-BPE-2.2 | 433 | 2-3 | | 700 | | | | | | |
| | | ABE-300 | 469 | 3 | | | 780 | 720 | 750 | 770 | 760 | 760 |
| | | A-BPE-4 | 513 | 4 | | | | | | | | |
| | | A-BPP-3 | 511 | 3 | | | | | | | | |
| | | BP-4PA | 569 | 4 | | | | | | | | |
| | | M-208 | 485 | 4 | | | | | | | | |

TABLE 7-continued

| | Components | Type | Mw | Number of ether bonds within one molecule | | | | | | | |
|---|---|---|---|---|---|---|---|---|---|---|---|
| | (C) | EG | 198 | 0 | | | 220 | | | | |
| | | SR212 | 198 | 0 | 300 | 300 | | 280 | | | |
| | | BG | 226 | 0 | | | | | 250 | | |
| | | FA-124AS | 198 | 0 | | | | | | 230 | |
| | | 1,6HX-A | 226 | 0 | | | | | | | 240 |
| | | 1,9ND-A | 268 | 0 | | | | | | | | 240 |
| | | NP-A | 212 | 0 | | | | | | | |
| | (A) | FA-222A | 214 | 1 | | | | | | | |
| | (B) | IB-XA | 208 | 0 | | | | | | | |
| | Initiator | Ir819 | | | 10 | 10 | 10 | 10 | 10 | 10 | 10 | 10 |
| | | Ir184 | | | | | | | | | |
| | | TPO | | | | | | | | | |
| Evaluation | Viscosity (mPa·s) | | | | 220 | 200 | 160 | 165 | 160 | 165 | 270 | 300 |
| | Flexural strength (MPa) | | | | 79 | 75 | 74 | 65 | 69 | 66 | 67 | 66 |
| | Flexural modulus (MPa) | | | | 2450 | 2230 | 2160 | 2020 | 2050 | 2045 | 2040 | 2015 |
| | Charpy impact strength (kJ/m$^2$) | | | | 1.0 | 1.0 | 1.0 | 1.3 | 1.1 | 1.1 | 1.2 | 1.3 |

| | Components | Type | Mw | Number of ether bonds within one molecule | Example 9C | Example 10C | Example 11C | Example 12C | Example 13C | Example 14C | Example 15C |
|---|---|---|---|---|---|---|---|---|---|---|---|
| Photocurable composition | (X) | A-BPE-2 | 424 | 2 | | | | | | | |
| | | A-BPE-2.2 | 433 | 2-3 | | | | | | | |
| | | ABE-300 | 469 | 3 | 680 | | | | | | |
| | | A-BPE-4 | 513 | 4 | | 750 | 690 | | | | |
| | | A-BPP-3 | 511 | 3 | | | | 750 | 750 | | |
| | | BP-4PA | 569 | 4 | | | | | | 750 | 750 |
| | | M-208 | 485 | 4 | | | | | | | |
| | (C) | EG | 198 | 0 | | 250 | | 250 | | 250 | |
| | | SR212 | 198 | 0 | | | | | | | |
| | | BG | 226 | 0 | | | | | 250 | | 250 |
| | | FA-124AS | 198 | 0 | | | | | | | |
| | | 1,6HX-A | 226 | 0 | | | | | | | |
| | | 1,9ND-A | 268 | 0 | | | | | | | |
| | | NP-A | 212 | 0 | 320 | | 310 | | | | |
| | (A) | FA-222A | 214 | 1 | | | | | | | |
| | (B) | IB-XA | 208 | 0 | | | | | | | |
| | Initiator | Ir819 | | | 10 | 10 | 10 | 10 | 10 | 10 | 10 |
| | | Ir184 | | | | | | | | | |
| | | TPO | | | | | | | | | |
| Evaluation | Viscosity (mPa·s) | | | | 160 | 220 | 160 | 330 | 310 | 280 | 260 |
| | Flexural strength (MPa) | | | | 66 | 72 | 65 | 71 | 66 | 68 | 65 |
| | Flexural modulus (MPa) | | | | 2030 | 2090 | 2015 | 2070 | 2055 | 2025 | 2010 |
| | Charpy impact strength (kJ/m$^2$) | | | | 1.1 | 1.0 | 1.2 | 1.1 | 1.3 | 1.2 | 1.3 |

TABLE 8

| | Components | Type | Mw | Number of ether bonds within one molecule | Example 16C | Example 17C | Example 18C | Example 19C | Example 20C | Example 21C |
|---|---|---|---|---|---|---|---|---|---|---|
| Photocurable composition | (X) | A-BPE-2 | 424 | 2 | | | | | | |
| | | A-BPE-2.2 | 433 | 2-3 | | | 700 | | | |
| | | ABE-300 | 469 | 3 | | | | 780 | | 780 |
| | | A-BPE-4 | 513 | 4 | | | | | 750 | |
| | | A-BPP-3 | 511 | 3 | | | | | | |
| | | BP-4PA | 569 | 4 | | | | | | |
| | | M-208 | 485 | 4 | 750 | 750 | | | | |
| | (C) | EG | 198 | 0 | 250 | | | 220 | 250 | 115 |
| | | SR212 | 198 | 0 | | | 300 | | | |
| | | BG | 226 | 0 | | 250 | | | | |
| | | FA-124AS | 198 | 0 | | | | | | |
| | | 1,6HX-A | 226 | 0 | | | | | | |
| | | 1,9ND-A | 268 | 0 | | | | | | |
| | | NP-A | 212 | 0 | | | | | | |
| | (A) | FA-222A | 214 | 1 | | | | | | 105 |
| | (B) | IB-XA | 208 | 0 | | | | | | |
| | Initiator | Ir819 | | | 10 | 10 | | | | 10 |
| | | Ir184 | | | | | 10 | 10 | 10 | |
| | | TPO | | | | | 10 | 10 | 10 | |

TABLE 8-continued

| Evaluation | | | | | | | | | |
|---|---|---|---|---|---|---|---|---|---|
| Viscosity (mPa·s) | | | | 90 | 85 | 210 | 170 | 240 | 170 |
| Flexural strength (MPa) | | | | 69 | 67 | 74 | 73 | 71 | 73 |
| Flexural modulus (MPa) | | | | 2055 | 2025 | 2240 | 2140 | 2080 | 2150 |
| Charpy impact strength (kJ/m²) | | | | 1.4 | 1.4 | 1.1 | 1.1 | 1.1 | 1.1 |

| | Components | Type | Mw | Number of ether bonds within one molecule | Example 22C | Example 23C | Example 24C | Example 25C | Example 26C |
|---|---|---|---|---|---|---|---|---|---|
| Photocurable composition | (X) | A-BPE-2 | 424 | 2 | | | | | |
| | | A-BPE-2.2 | 433 | 2-3 | | | | | |
| | | ABE-300 | 469 | 3 | 780 | 780 | 770 | 770 | 770 |
| | | A-BPE-4 | 513 | 4 | | | | | |
| | | A-BPP-3 | 511 | 3 | | | | | |
| | | BP-4PA | 569 | 4 | | | | | |
| | | M-208 | 485 | 4 | | | | | |
| | (C) | EG | 198 | 0 | 115 | 115 | | | |
| | | SR212 | 198 | 0 | | | | | |
| | | BG | 226 | 0 | | | | | |
| | | FA-124AS | 198 | 0 | | | 120 | 120 | 120 |
| | | 1,6HX-A | 226 | 0 | | | | | |
| | | 1,9ND-A | 268 | 0 | | | | | |
| | | NP-A | 212 | 0 | | | | | |
| | (A) | FA-222A | 214 | 1 | 55 | | 110 | 55 | |
| | (B) | IB-XA | 208 | 0 | 50 | 105 | | 55 | 110 |
| | Initiator | Ir819 | | | 10 | 10 | 10 | 10 | 10 |
| | | Ir184 | | | | | | | |
| | | TPO | | | | | | | |
| Evaluation | Viscosity (mPa·s) | | | | 190 | 220 | 180 | 200 | 230 |
| | Flexural strength (MPa) | | | | 74 | 76 | 68 | 70 | 73 |
| | Flexural modulus (MPa) | | | | 2150 | 2160 | 2090 | 2100 | 2120 |
| | Charpy impact strength (kJ/m²) | | | | 1.0 | 1.0 | 1.1 | 1.1 | 1.1 |

TABLE 9

| | Components | Type | Mw | Number of ether bonds within one molecule | Comparative Example 1C | Comparative Example 2C | Comparative Example 3C | Comparative Example 4C | Comparative Example 5C |
|---|---|---|---|---|---|---|---|---|---|
| Photocurable composition | (X) | A-BPE-2 | 424 | 2 | | | | | |
| | | A-BPE-2.2 | 433 | 2-3 | | | | | |
| | | ABE-300 | 469 | 3 | | | | | |
| | | A-BPE-4 | 513 | 4 | | | | | |
| | | A-BPP-3 | 511 | 3 | | | | | |
| | | BP-4PA | 569 | 4 | | | | | |
| | | M-208 | 485 | 4 | | | | | |
| | (C) | EG | 198 | 0 | 250 | 250 | 200 | | |
| | | SR212 | 198 | 0 | | | | | |
| | | BG | 226 | 0 | | | | | |
| | | FA-124AS | 198 | 0 | | | | | |
| | | 1,6HX-A | 226 | 0 | | | | 200 | |
| | | 1,9ND-A | 268 | 0 | | | | | 200 |
| | | NP-A | 212 | 0 | | | | | |
| | (A) | FA-222A | 214 | 1 | | | | | |
| | (B) | IB-XA | 208 | 0 | | | | | |
| | Other monomer | A-BPE-10 | 777 | 10 | 750 | | | | |
| | | A-BPE-20 | 1217 | 20 | | 750 | | | |
| | | BP-2EM | 479 | 2-3 | | | 800 | 800 | 800 |
| | | 1,10DD | 282 | 0 | | | | | |
| | | EGDA | 170 | 0 | | | | | |
| | | 1,12DDDA | 310 | 0 | | | | | |
| | | 1,10DDMA | 310 | 0 | | | | | |
| | Initiator | Ir819 | | | 10 | 10 | 10 | 10 | 10 |
| | | Ir184 | | | | | | | |
| | | TPO | | | | | | | |
| Evaluation | Viscosity (mPa·s) | | | | 170 | 160 | 120 | 130 | 140 |
| | Flexural strength (MPa) | | | | 40 | 28 | 75 | 71 | 68 |
| | Flexural modulus (MPa) | | | | 1030 | 720 | 2850 | 2640 | 2525 |
| | Charpy impact strength (kJ/m²) | | | | 2.2 | 2.3 | 0.5 | 0.6 | 0.6 |

TABLE 9-continued

| Components | | Type | Mw | Number of ether bonds within one molecule | Comparative Example 6C | Comparative Example 7C | Comparative Example 8C | Comparative Example 9C |
|---|---|---|---|---|---|---|---|---|
| Photocurable composition | (X) | A-BPE-2 | 424 | 2 | | | | |
| | | A-BPE-2.2 | 433 | 2-3 | | | | |
| | | ABE-300 | 469 | 3 | 700 | 800 | 740 | 700 |
| | | A-BPE-4 | 513 | 4 | | | | |
| | | A-BPP-3 | 511 | 3 | | | | |
| | | BP-4PA | 569 | 4 | | | | |
| | | M-208 | 485 | 4 | | | | |
| | (C) | EG | 198 | 0 | | | | |
| | | SR212 | 198 | 0 | | | | |
| | | BG | 226 | 0 | | | | |
| | | FA-124AS | 198 | 0 | | | | |
| | | 1,6HX-A | 226 | 0 | | | | |
| | | 1,9ND-A | 268 | 0 | | | | |
| | | NP-A | 212 | 0 | | | | |
| | (A) | FA-222A | 214 | 1 | | | | |
| | (B) | IB-XA | 208 | 0 | | | | |
| | Other monomer | A-BPE-10 | 777 | 10 | | | | |
| | | A-BPE-20 | 1217 | 20 | | | | |
| | | BP-2EM | 479 | 2-3 | | | | |
| | | 1,10DD | 282 | 0 | 300 | | | |
| | | EGDA | 170 | 0 | | 200 | | |
| | | 1,12DDDA | 310 | 0 | | | 260 | |
| | | 1,10DDMA | 310 | 0 | | | | 300 |
| | Initiator | Ir819 | | | 10 | 10 | 10 | 10 |
| | | Ir184 | | | | | | |
| | | TPO | | | | | | |
| Evaluation | | Viscosity (mPa·s) | | | 250 | 160 | 340 | 300 |
| | | Flexural strength (MPa) | | | 56 | 76 | 52 | 61 |
| | | Flexural modulus (MPa) | | | 1765 | 2215 | 1465 | 1970 |
| | | Charpy impact strength (kJ/m$^2$) | | | 1.3 | 0.9 | 1.5 | 0.7 |

—Description of Tables 7 to 9—

In Tables 7 to 9, each of the acrylic monomers (X) is the same as that described in the "Description of Tables 1 to 3" above.

The respective structures of the (meth)acrylic monomers (C) listed in Tables 7 to 9 are as shown below.

EG, BG and NP-A are methacrylic monomers manufactured by Kyoeisha Chemical Co. Ltd.; SR212 is an acrylic monomer manufactured by Arkema Inc.; FA-124AS is an acrylic monomer manufactured by Hitachi Chemical Co., Ltd.; and 1,6HX-A and 1,9ND-A are acrylic monomers manufactured by Kyoeisha Chemical Co. Ltd.

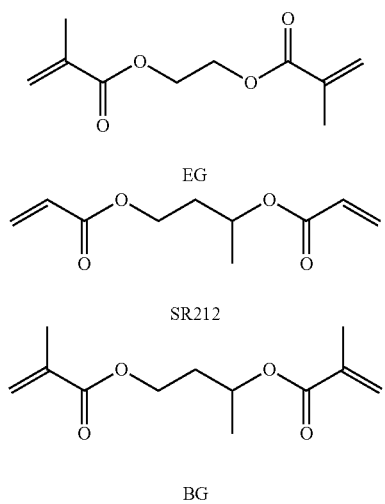

EG

SR212

BG

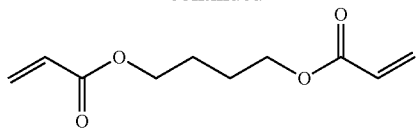

FA-124AS

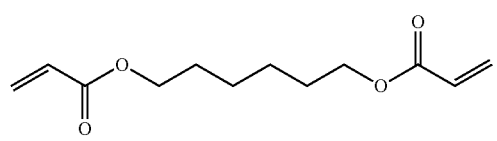

1,6HX-A

NP-A

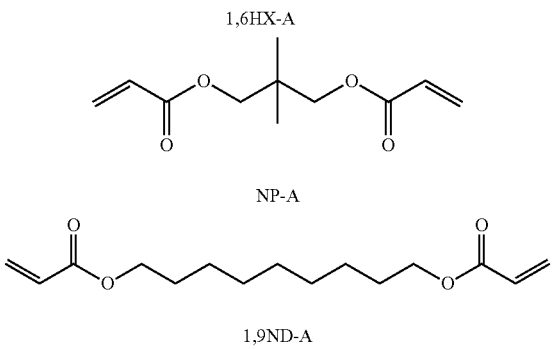

1,9ND-A

In Tables 7 to 9, each of FA-222A, which is the (meth)acrylic monomer (A), and IB-XA, which is the (meth)acrylic monomer (B), has the same structure as that described in the "Description of Tables 1 to 3" above.

Of the other (meth)acrylic monomers listed in Tables 7 to 9, each of A-BPE-10, A-BPE-20, and BP-2EM is the same as that described in the "Description of Tables 1 to 3" above.

The rest of the (meth)acrylic monomers listed in Tables 7 to 9, other than those described above, have the structure as shown below.

1,10DD and 1,10DDMA are "A-DOD-N", which is an acrylic monomer manufactured by Shin Nakamura Chemical Co., Ltd, and "DOD-N", which is a methacrylic monomer manufactured by Shin Nakamura Chemical Co., Ltd., respectively.

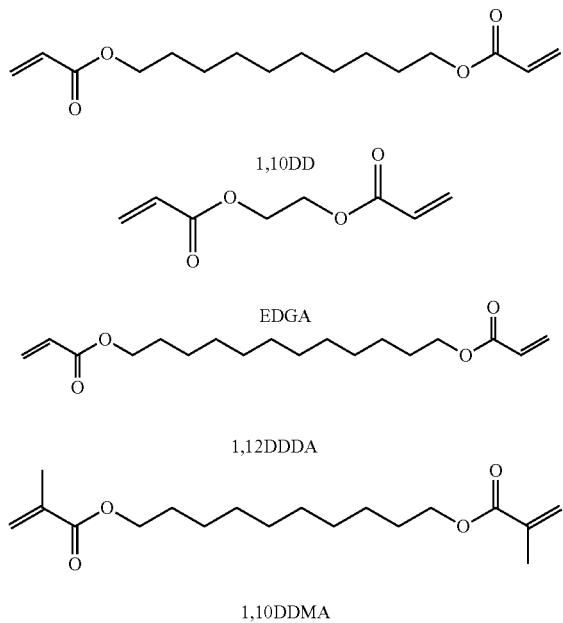

In Tables 7 to 9, the term "Initiator" denotes photopolymerization initiators.

Each of the initiators (namely, the photopolymerization initiators) listed in Tables 7 to 9 is the same as that described in the "Description of Tables 1 to 3" above.

As shown in Tables 7 to 9, in each of Examples 1C to 26C, a photocurable composition was used which includes: the acrylic monomer (X) which is a diacrylic monomer containing two aromatic rings and two acryloyloxy groups within one molecule, and having a weight average molecular weight of from 400 to 580; the (meth)acrylic monomer (C) which is a di(meth)acrylic monomer not containing an aromatic ring and containing a hydrocarbon skeleton and two (meth)acryloyloxy groups within one molecule, and having a weight average molecular weight of from 190 to 280; and the photopolymerization initiator. As a result, it was possible to obtain a stereolithographed product which satisfies all of: a flexural strength of 60 MPa or more, a flexural modulus of 1,500 MPa or more, and a Charpy impact strength of 1.0 kJ/m$^2$ or more, in each of Examples 1C to 26C. Further, the photocurable compositions of Examples 1C to 26C had a viscosity suitable for stereolithography.

The above results confirmed that each of the photocurable compositions of Examples 1C to 26C is suitable for the production by stereolithography of a dental prosthesis or the like (a denture base, in particular).

In contrast to Examples 1C to 26C, in Comparative Examples 1C and 2C, in each of which a diacrylic monomer (A-BPE-10 or A-BPE-20) containing two aromatic rings and two acryloyloxy groups within one molecule and having a weight average molecular weight of greater than 580 was used instead of the acrylic monomer (X), the resulting stereolithographed products had an insufficient flexural strength and flexural modulus.

In Comparative Examples 3C to 5C, in each of which BP-2EM, which is a methacrylic monomer, not an acrylic monomer, containing two aromatic rings and two methacryloyloxy groups within one molecule and having a weight average molecular weight of from 400 to 580, was used instead of the acrylic monomer (X), the resulting stereolithographed products had an insufficient Charpy impact strength.

In Comparative Examples 6C, 8C and 9C, in each of which a di(meth)acrylic monomer (1,10DD, 1,12DDDA, or 1,10DDMA) not containing an aromatic ring and containing a hydrocarbon skeleton and two (meth)acryloyloxy groups within one molecule, and having a weight average molecular weight of greater than 280, was used instead of the (meth) acrylic monomer (C), the flexural strength and the flexural modulus of the resulting stereolithographed products were reduced, as compared to those of Examples 1C to 26C.

In Comparative Example 9C, the Charpy impact strength of the resulting stereolithographed product was also reduced, as compared to that of Examples 1C to 26C.

Further, in Comparative Example 7C, in which a diacrylic monomer (EGDA) not containing an aromatic ring and containing a hydrocarbon skeleton and two (meth)acryloyloxy groups within one molecule, and having a weight average molecular weight of less than 190, was used instead of the (meth)acrylic monomer (C), the resulting stereolithographed product had an insufficient Charpy impact strength.

The disclosures of Japanese Patent Application No. 2015-019541, Japanese Patent Application No. 2015-019542, and Japanese Patent Application No. 2015-019543 are incorporated herein by reference in their entirety.

All publications, patent applications, and technical standards mentioned in the present specification are incorporated herein by reference to the same extent as if such individual publication, patent application, or technical standard was specifically and individually indicated to be incorporated by reference.

The invention claimed is:

1. A photocurable composition that is used for production by stereolithography of a dental prosthesis, a medical device for intraoral use, or a tooth and/or jaw model, the photocurable composition comprising:
a (meth)acrylic monomer component and a photopolymerization initiator;
wherein the (meth)acrylic monomer component comprises:
an acrylic monomer (X) that is at least one selected from diacrylic monomers containing, within one molecule, two aromatic rings and two acryloyloxy groups, and that has a weight average molecular weight of from 400 to 580; and
at least one selected from the group consisting of:
a (meth)acrylic monomer (A) that is at least one selected from di(meth)acrylic monomers not containing, within one molecule, an aromatic ring and containing, within one molecule, one or more ether bonds and two (meth)acryloyloxy groups, and that has a weight average molecular weight of from 200 to 400;
a (meth)acrylic monomer (B) that is at least one selected from (meth)acrylic monomers not containing, within one molecule, an aromatic ring and containing, within one molecule, a ring structure other than an aromatic ring and one (meth)acryloyloxy group, and that has a weight average molecular weight of from 130 to 240; and a (meth)acrylic monomer (C) that is at least one selected from di(meth)acrylic monomers not containing, within one molecule, an aromatic ring or an ether bond and containing, within one molecule, a hydrocarbon skeleton and two (meth) acryloyloxy groups, and that has a weight average molecular weight of from 190 to 280, and wherein the photopolymerization initiator is at least one selected from alkylphenone compounds or acylphosphine oxide compounds.

2. The photocurable composition according to claim 1, wherein at least one of the diacrylic monomers constituting the acrylic monomer (X) contains an ether bond within one molecule.

3. The photocurable composition according to claim 1, wherein at least one of the diacrylic monomers constituting the acrylic monomer (X) contains from one to four ether bonds within one molecule.

4. The photocurable composition according to claim 1, wherein at least one of the diacrylic monomers constituting the acrylic monomer (X) is a compound represented by the following Formula (x-1):

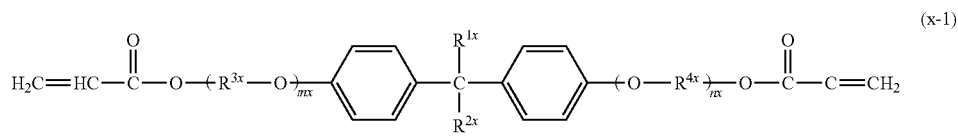

(x-1)

wherein, in Formula (x-1), each of $R^{1x}$ and $R^{2x}$ independently represents a hydrogen atom or a methyl group; each of $R^{3x}$ and $R^{4x}$ independently represents a straight chain or branched chain alkylene group having from 2 to 4 carbon atoms; and each of mx and nx independently represents a number from 0 to 4, and wherein mx and nx satisfy: $1 \leq (mx+nx) \leq 4$.

5. The photocurable composition according to claim 1, wherein at least one of the diacrylic monomers constituting the acrylic monomer (X) is a compound represented by the following Formula (x-2):

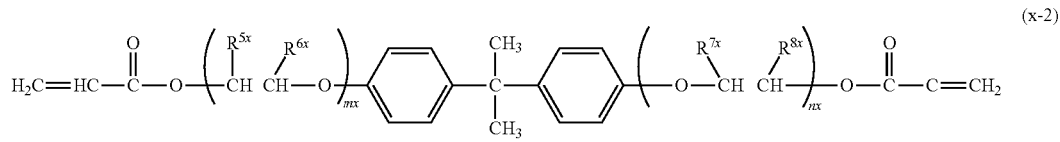

(x-2)

wherein, in Formula (x-2), each of $R^{5x}$, $R^{6x}$, $R^{7x}$, and $R^{8x}$ independently represents a hydrogen atom or a methyl group; and each of mx and nx independently represents a number from 0 to 4, and wherein mx and nx satisfy: $1 \leq (mx+nx) \leq 4$.

6. The photocurable composition according to claim 1, wherein at least one of the di(meth)acrylic monomers constituting the (meth)acrylic monomer (A) is a compound represented by the following Formula (a-1):

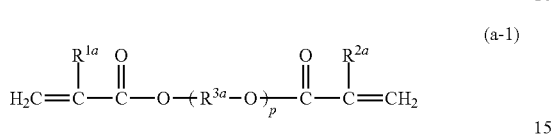

(a-1)

wherein, in Formula (a-1), each of $R^{1a}$ and $R^{2a}$ independently represents a hydrogen atom or a methyl group; each lea independently represents a straight chain or branched chain alkylene group having from 2 to 4 carbon atoms; and p represents a number from 2 to 4.

7. The photocurable composition according to claim 1, wherein at least one of the di(meth)acrylic monomers constituting the (meth)acrylic monomer (A) is a compound represented by the following Formula (a-2):

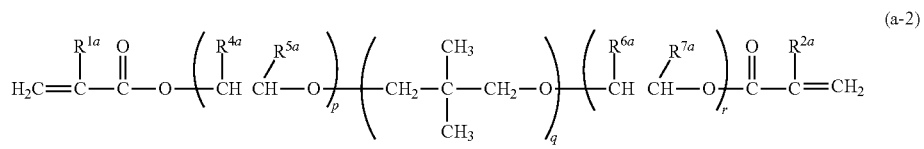

(a-2)

wherein, in Formula (a-2), each of $R^{1a}$, $R^{2a}$, $R^{4a}$, $R^{5a}$, $R^{6a}$, and $R^{7a}$ independently represents a hydrogen atom or a methyl group; and each of p, q, and r independently represents 0 or 1, and wherein p, q, and r satisfy: $p+q+r \geq 2$.

8. The photocurable composition according to claim 1, wherein at least one of the (meth)acrylic monomers constituting the (meth)acrylic monomer (B) is a compound represented by the following Formula (b-1):

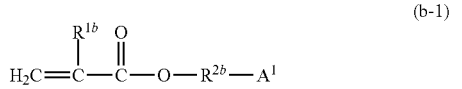

(b-1)

wherein, in Formula (b-1), $R^{1b}$ represents a hydrogen atom or a methyl group; $R^{2b}$ represents a single bond or a methylene group; and $A^1$ represents a ring structure other than an aromatic ring.

9. The photocurable composition according to claim 1, wherein at least one of the (meth)acrylic monomers constituting the (meth)acrylic monomer (B) is a compound represented by the following Formula (b-2):

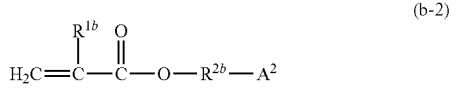

(b-2)

wherein, in Formula (b-2), $R^{1b}$ represents a hydrogen atom or a methyl group; $R^{2b}$ represents a single bond or a methylene group; and $A^2$ represents a ring structure containing a dicyclopentenyl skeleton, a dicyclopentanyl skeleton, a cyclohexane skeleton, a tetrahydrofuran skeleton, a morpholine skeleton, an isobornyl skeleton, a norbornyl skeleton, a dioxolane skeleton, or a dioxane skeleton.

10. The photocurable composition according to claim 1, wherein at least one of the di(meth)acrylic monomers constituting the (meth)acrylic monomer (C) is a compound represented by the following Formula (c-1):

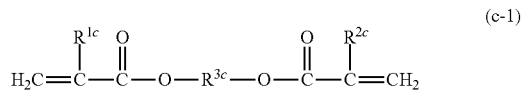

(c-1)

wherein, in Formula (c-1), each of $R^{1c}$ and $R^{2c}$ independently represents a hydrogen atom or a methyl group; and $R^{3'}$ represents an alkylene group having from 1 to 9 carbon atoms.

11. The photocurable composition according to claim 1, wherein at least one of the di(meth)acrylic monomers constituting the (meth)acrylic monomer (C) is a compound represented by the following Formula (c-2):

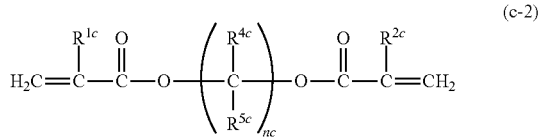

(c-2)

wherein, in Formula (c-2), each of $R^{1c}$ and $R^{2c}$ independently represents a hydrogen atom or a methyl group; each of $R^{4c}$ and $R^{5c}$ independently represents a hydrogen atom or a methyl group; and nc represents a number from 1 to 9, and wherein an alkylene group represented by $-(CR^{4c}R^{5c})_{nc}-$ has from 1 to 9 carbon atoms.

12. The photocurable composition according to claim 1, wherein a content of the acrylic monomer (X) is from 550 parts by mass to 800 parts by mass with respect to 1,000 parts by mass of a total content of the (meth)acrylic monomer component.

13. The photocurable composition according to claim 1, wherein a content of the (meth)acrylic monomer (A) is from 100 parts by mass to 450 parts by mass with respect to 1,000 parts by mass of a total content of the (meth)acrylic monomer component.

14. The photocurable composition according to claim 1, wherein a content of the (meth)acrylic monomer (B) is from 100 parts by mass to 450 parts by mass with respect to 1,000 parts by mass of a total content of the (meth)acrylic monomer component.

15. The photocurable composition according to claim 1, wherein a content of the (meth)acrylic monomer (C) is from 100 parts by mass to 450 parts by mass with respect to 1,000 parts by mass of a total content of the (meth)acrylic monomer component.

16. The photocurable composition according to claim 1, wherein a content of the photopolymerization initiator is from 1 part by mass to 50 parts by mass with respect to 1,000 parts by mass of a total content of the (meth)acrylic monomer component.

17. The photocurable composition according to claim 1, wherein the photocurable composition has a viscosity, as measured using a Type E viscometer at 25° C. and 50 rpm, of from 20 mPa·s to 1500 mPa·s.

18. The photocurable composition according to claim 1, which is used for the production by stereolithography of a denture base or a mouthpiece.

19. The photocurable composition according to claim 1, which is used for the production by stereolithography of a denture base.

20. A method for producing a dental prosthesis, a medical device for intraoral use, or a tooth and/or jaw model by stereolithography, the method comprising: photocuring the photocurable composition according to claim 1.

* * * * *